(12) United States Patent
Jackson et al.

(10) Patent No.: US 9,593,134 B2
(45) Date of Patent: Mar. 14, 2017

(54) COMPLEXES USEFUL AS ACTIVE COMPONENTS IN SUPPORTED EPOXIDATION CATALYSTS

(71) Applicant: Lyondell Chemical Technology, L.P., Houston, TX (US)

(72) Inventors: Debra L. Jackson, Huffman, TX (US); Barbara Kimmich, Houston, TX (US); Ilya E. Nifant'ev, Moscow (RU); Sandor Nagy, Webster, TX (US); Daniel F. White, Houston, TX (US); Pavel V. Ivchenko, Moscow (RU)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 14/801,477

(22) Filed: Jul. 16, 2015

(65) Prior Publication Data

US 2016/0016157 A1 Jan. 21, 2016

Related U.S. Application Data

(60) Provisional application No. 62/026,295, filed on Jul. 18, 2014.

(51) Int. Cl.
 *C07F 7/08* (2006.01)
 *C07F 7/28* (2006.01)
 (Continued)

(52) U.S. Cl.
 CPC ......... *C07F 7/0816* (2013.01); *B01J 31/0212* (2013.01); *B01J 31/0214* (2013.01);
 (Continued)

(58) Field of Classification Search
 CPC ........ C07F 7/003; C07F 7/006; C07F 7/0807; C07F 7/12; C07F 7/28; B01J 31/1625; B01J 31/0212; B01J 31/2295; B01J 31/0214
 (Continued)

(56) References Cited

U.S. PATENT DOCUMENTS 5,977,009 A 11/1999 Faraj
6,355,596 B2 3/2002 Hu et al.
(Continued)

FOREIGN PATENT DOCUMENTS

WO WO-03101977 A1 12/2003

OTHER PUBLICATIONS

Duff et al., Journal of the Chemical Society, Dalton Transactions: Inorganic Chemistry (1972-1999), (3), pp. 489-498 (1986).*
(Continued)

*Primary Examiner* — Porfirio Nazario Gonzalez

(57) ABSTRACT

Method of preparing epoxidation catalysts are disclosed, including methods comprising reacting an inorganic siliceous solid with a metal complex of the formulas:

$$\begin{array}{c} L_1 \diagdown_{Ti} \diagup L_2 \\ \diagup \quad \diagdown \\ X_1 \quad X_2 \end{array} \quad (I)$$

$$\begin{array}{c} L_1 \diagdown_{Ti} \diagup L_2 \\ \diagup \quad \diagdown \\ X_1 \quad L_3 \end{array} \quad (II)$$

(Continued)

-continued

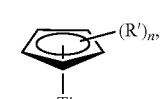 (III)

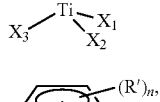

(IV)

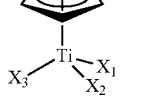

(V)

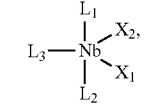

(VI)

wherein the variables are defined herein.

22 Claims, 4 Drawing Sheets

(51) Int. Cl.
C07F 9/00 (2006.01)
B01J 31/16 (2006.01)
C07F 7/00 (2006.01)
B01J 31/02 (2006.01)
B01J 31/22 (2006.01)

(52) U.S. Cl.
CPC ....... B01J 31/1625 (2013.01); B01J 31/2295 (2013.01); C07F 7/006 (2013.01); C07F 7/0809 (2013.01); C07F 7/28 (2013.01); C07F 9/005 (2013.01); B01J 2231/72 (2013.01); B01J 2531/46 (2013.01); B01J 2531/57 (2013.01)

(58) Field of Classification Search
USPC ............................... 556/11, 12, 42, 406, 489
See application file for complete search history.

(56) References Cited

U.S. PATENT DOCUMENTS 6,759,541 B2  7/2004  Grey
2016/0152738 A1*  6/2016  Jingwen ................. C08F 4/025
                                                      526/123.1

OTHER PUBLICATIONS

Chemical Abstract compounds, STN express.
Fraile, J.M. et al., Titanium catalysts supported on silica. X-ray absorption investigation on their structures and comparison of their catalytic activities in Diels-Alder and epoxidation reactions, The Journal of Physical Chemistry, 1996, vol. 100, No. 50, pp. 19484-19488.
The International Search Report and Written Opinion for PCT/US2015/040784 mailed Sep. 13, 2016.

* cited by examiner

COMPLEXES USEFUL AS ACTIVE COMPONENTS IN SUPPORTED EPOXIDATION CATALYSTS

BACKGROUND OF THE INVENTION

I. Field of the Invention

The present invention relates generally to the preparation of transition metal on silica catalysts, such as titanated silica catalysts that may be used for the epoxidation of olefins to epoxides.

II. Description of Related Art

Catalysts may be utilized in connection with many reactions, including the epoxidation of olefins. Improving the properties of these catalysts, including their stability, activity, and selectivity remains a useful and desirable goal.

SUMMARY OF THE INVENTION

In one aspect, there are provided methods of preparing catalysts, comprising:

(a) contacting an inorganic siliceous solid with a metal complex of the formula:

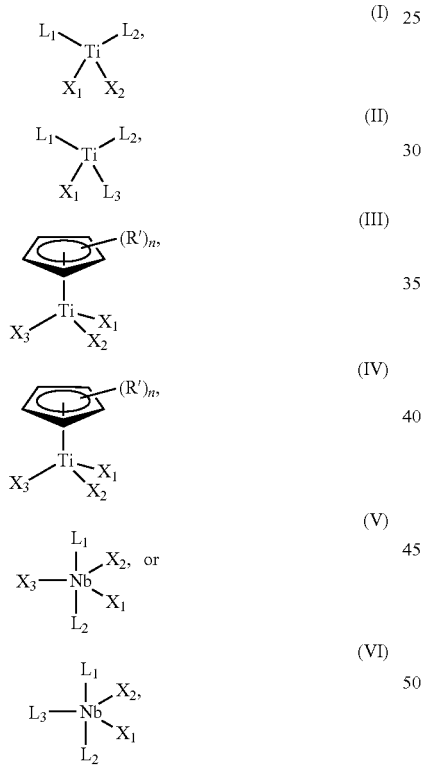

wherein:
$L_1$ is alkoxy$_{(C≤8)}$, aryloxy$_{(C≤16)}$, aralkoxy$_{(C≤16)}$, or a substituted version of any of these groups, or $L_1$ is taken together with $L_2$ as defined below, or $L_1$ is taken together with $L_2$ and $L_3$ as defined below;
$L_2$ is alkoxy$_{(C≤8)}$, aryloxy$_{(C≤16)}$, aralkoxy$_{(C≤16)}$, or a substituted version of any of these groups, or $L_2$ is taken together with $L_1$ as defined below, or $L_2$ is taken together with $L_1$ and $L_3$ as defined below;
$L_3$, if present, is alkoxy$_{(C≤8)}$, aryloxy$_{(C≤16)}$, aralkoxy$_{(C≤16)}$, or a substituted version of any of these groups, or $L_3$ is taken together with $L_1$ and $L_2$ as defined below:

$L_1$ and $L_2$, when taken together, are a group of the formula:

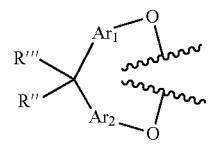

wherein:
$R''$ and $R'''$ are each independently —H, alkyl$_{(C≤8)}$, alkenyl$_{(C≤8)}$, alkynyl$_{(C≤8)}$, aryl$_{(C≤12)}$, aralkyl$_{(C≤12)}$, heteroaryl$_{(C≤8)}$, heterocycloalkyl$_{(C≤12)}$, or a substituted versions of any of these groups other than —H; and
$Ar_1$ and $Ar_2$ are each independently arenediyl$_{(C≤16)}$ or substituted arenediyl$_{(C≤16)}$;
$L_1$, $L_2$ and $L_3$, when taken together, are a group of the formula:

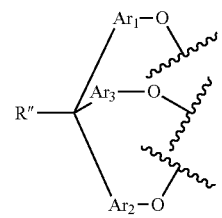

wherein:
$R''$ is —H, alkyl$_{(C≤8)}$, alkenyl$_{(C≤8)}$, alkynyl$_{(C≤8)}$, aryl$_{(C≤12)}$, aralkyl$_{(C≤12)}$, heteroaryl$_{(C≤8)}$, heterocycloalkyl$_{(C≤12)}$, or a substituted versions of any of these groups other than —H; and
$Ar_1$, $Ar_2$, and $Ar_3$ are each independently arenediyl$_{(C≤16)}$ or substituted arenediyl$_{(C≤16)}$;
$X_1$, $X_2$, and $X_3$ are each chloro;
$R'$ is each independently:
—H, —OH, —SH, —CN, —F, —CF$_3$, —NH$_2$, —Si(CH$_3$)$_2$Cl, or —Si(CH$_3$)$_2$—Cp-Si(CH$_3$)$_2$Cl; or
alkyl$_{(C≤8)}$, alkenyl$_{(C≤8)}$, alkynyl$_{(C≤8)}$, aryl$_{(C≤12)}$, aralkyl$_{(C≤12)}$, heteroaryl$_{(C≤8)}$, heterocycloalkyl$_{(C≤12)}$, or a substituted versions of any of these groups; or
two or more pairs of R' are taken together to form an alkenediyl$_{(C≤8)}$ or a substituted alkenediyl$_{(C≤8)}$; and
n is 0 to 5;
to form a metal complex inorganic siliceous solid mixture; and (b) calcining the mixture from step (a) between 200° C. to 400° C. under conditions suitable to form a catalyst comprising the metal from the metal complex attached to the inorganic siliceous solid;
with the proviso that the method does not comprise a calcining step at a temperature greater than 400° C.

In some embodiments, the metal complex is of formula (I). In other embodiments, the metal complex is of formula (II). In yet other embodiments, the metal complex is of formula (III). In still other embodiments, the metal complex is of formula (IV).

In some embodiments, $L_1$, $L_2$, or $L_3$ is aryloxy$_{(C≤16)}$, for example, 2,6-diisopropylphenoxy or 2,6-di-tert-butyl-(4- methyl)-phenoxy. In some embodiments, $L_1$, $L_2$, or $L_3$ is alkoxy$_{(C \leq 8)}$, for example, isopropoxy.

In some embodiments, $L_1$ and $L_2$ are taken together and are a group of the formula:

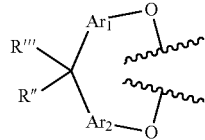

wherein: R″ and R‴ are each independently —H, substituted alkyl$_{(C \leq 8)}$, alkenyl$_{(C \leq 8)}$, or a substituted aryl$_{(C \leq 12)}$; and $Ar_1$ and $Ar_2$ are each independently arenediyl$_{(C \leq 16)}$.

In some embodiments, $L_1$, $L_2$ and $L_3$ are taken together and are a group of the formula:

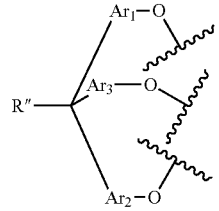

wherein: R‴ is —H or a substituted aryl$_{(C \leq 12)}$; and $Ar_1$ and $Ar_2$ are each independently arenediyl$_{(C \leq 16)}$.

In some embodiments, R' is —Si(CH$_3$)$_2$Cl.

In some embodiments, step (a) is conducted in the presence of a halogenated hydrocarbon. In some embodiments, the halogenated hydrocarbon is methylene chloride.

In some embodiments, the methods further comprise a cross-linking step, whereby $L_1$, $L_2$, or $L_3$ attached to a first metal site of the catalyst is connected with an $L_1$, $L_2$, or $L_3$ attached to a second metal site of the catalyst.

In some embodiments, the resulting catalyst has an activity for the epoxidation of 1-octene that is greater than 1.5 grams of tert-butylhydroperoxide (TBHP) reacted per gram of catalyst per hour when 14 mL of 1-octene solution of 41% tert-butylhydroperoxide (TBHP) in tert-butyl alcohol (4.4 wt. % TBHP in 1-octene) is stirred under nitrogen at 80° C.

In another aspect, there are provided methods of preparing a stabilized catalyst, comprising:

(a) contacting an inorganic siliceous solid with titanium tetrachloride to produce a titanium tetrachloride-impregnated solid;

(b) calcining the titanium tetrachloride-impregnated solid at a temperature from 500° C. to 1000° C. to produce a pre-catalyst;

(d) reacting the pre-catalyst with a compound of the formula:

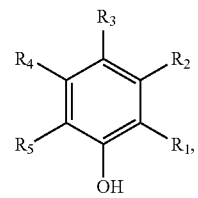

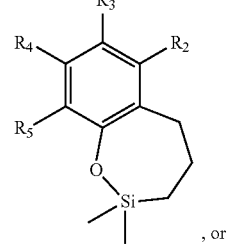

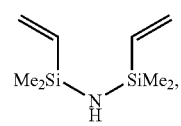

wherein:
$R_1$, $R_2$, $R_3$, $R_4$, and $R_5$ are each independently is each independently:
—H, —OH, —F, —CF$_3$, —NH$_2$, or —Si(CH$_3$)$_2$Cl; or
alkyl$_{(C \leq 8)}$, alkenyl$_{(C \leq 8)}$, alkynyl$_{(C \leq 8)}$, aryl$_{(C \leq 12)}$, aralkyl$_{(C \leq 12)}$, heteroaryl$_{(C \leq 8)}$, acyl$_{(C \leq 8)}$, alkoxy$_{(C \leq 8)}$, aryloxy$_{(C \leq 12)}$, acyloxy$_{(C \leq 8)}$, alkylamino$_{(C \leq 8)}$, dialkylamino$_{(C \leq 8)}$, amido$_{(C \leq 8)}$, or substituted versions of any of these groups;
at 100° C. to 300° C. and under conditions suitable for forming the stabilized catalyst.

In some embodiments, $R_1$, $R_2$, $R_3$, $R_4$, and $R_5$ are each —H.

In some embodiments, step (a) further comprises adding an inorganic siliceous solid to a column to produce a solid-filled column and adding to the solid-filled column a solution comprising the titanium tetrachloride and a hydrocarbon solvent to produce the titanium tetrachloride-impregnated solid.

In some embodiments, the methods further comprise a cross-linking step, whereby the stabilized catalyst comprises two or more alkenyl$_{(C \leq 8)}$ groups that react with one another to form a covalent bond when the catalyst is heated at 400° C. to 800° C.

In another aspect, there are provided metal complexes of the formula:

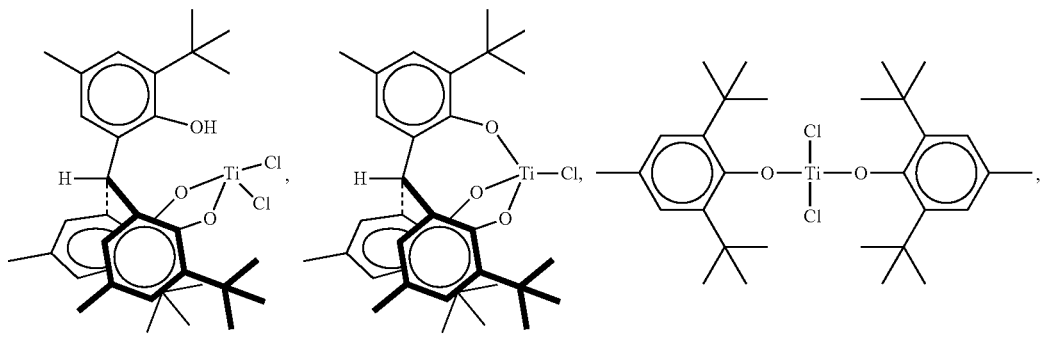

-continued

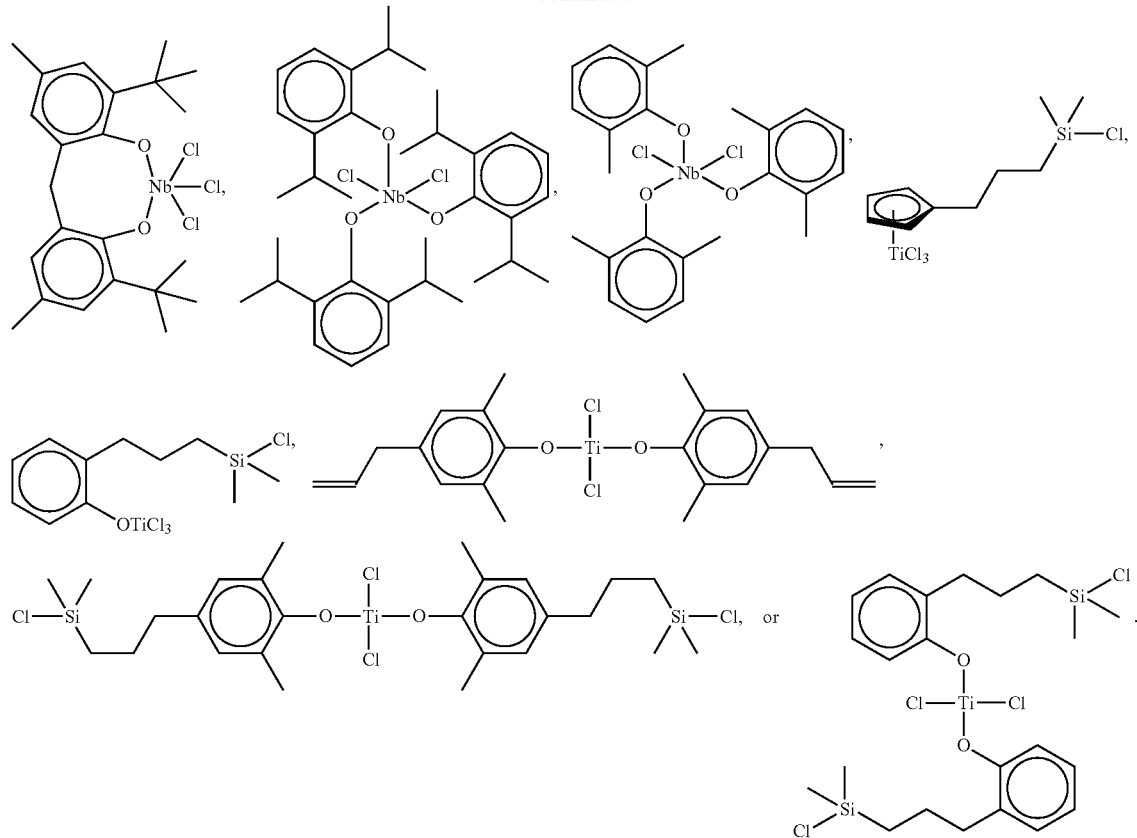

In another aspect there are provided compounds of the formula:

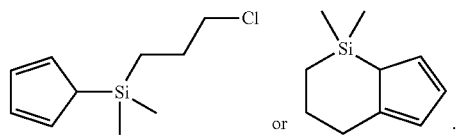

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

The following drawings form part of the present specification and are included to further demonstrate certain aspects of the present disclosure. The invention may be better understood by reference to one of these drawings in combination with the detailed description of specific embodiments presented herein.

DESCRIPTION OF ILLUSTRATIVE EMBODIMENTS

I. Epoxidation

Figure 1:
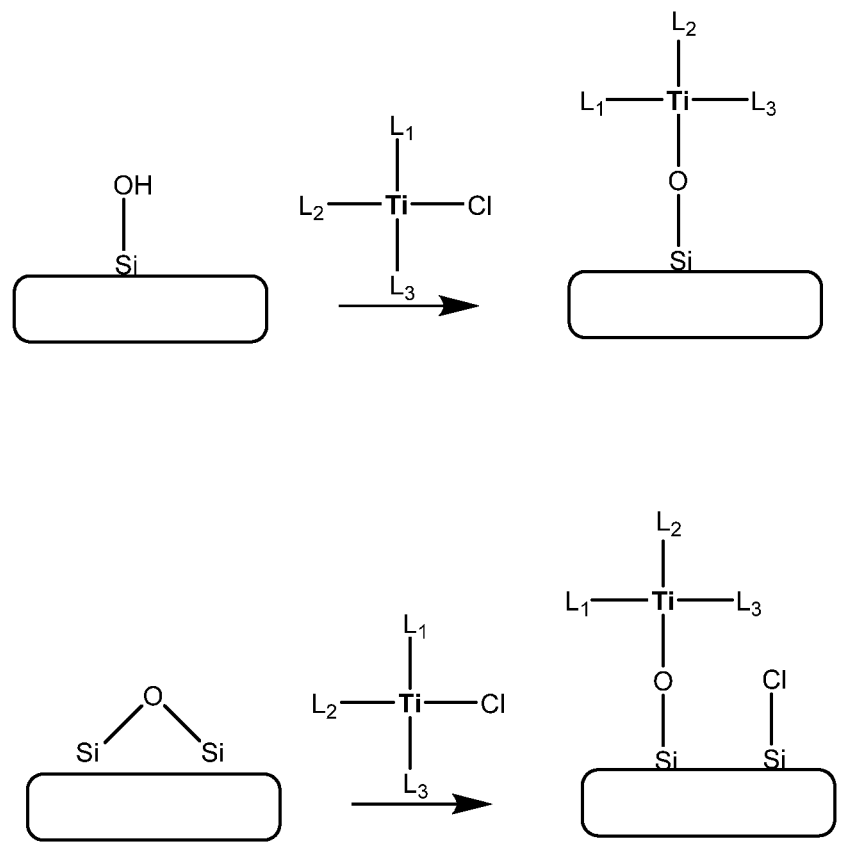
FIG. 1 shows two examples of reactions between a titanium complex and a metal surface that may be used to prepare a silica-supported titanium epoxidation catalyst. $L_1$, $L_2$, and $L_3$ represent ligands. These may be the same or different. In some embodiments, one or more of $L_1$, $L_2$, and $L_3$ may be connected to one another so as to form bidentate or tridentate ligands.
Figure 2:
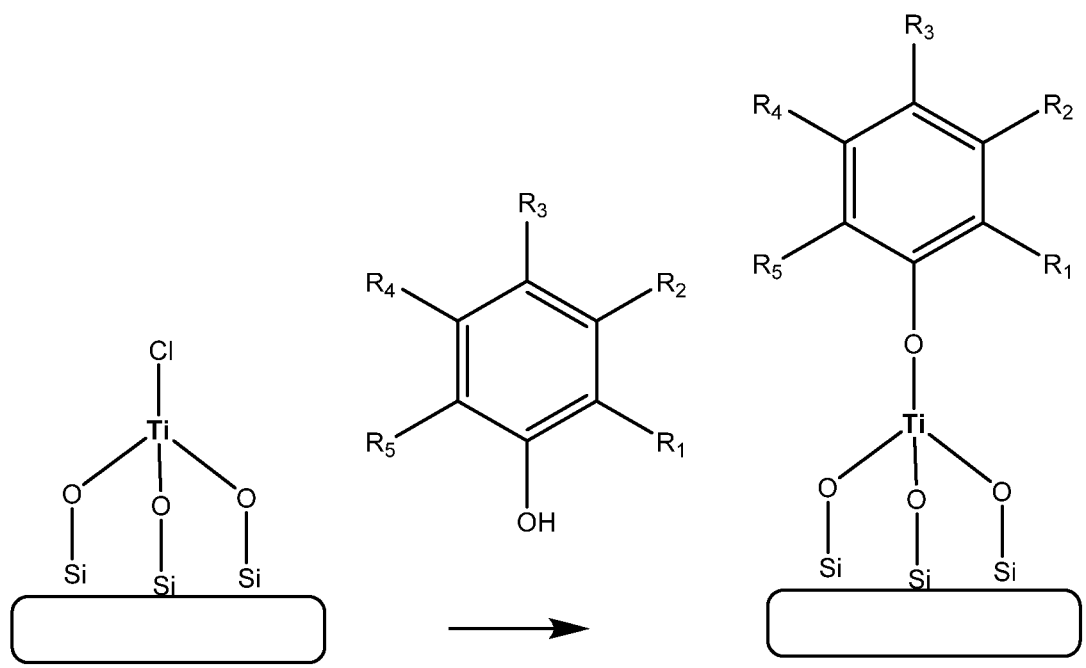
FIG. 2 shows an example of a reaction occurring between an optionally substituted phenol and a reactive Ti—X center attached to a silica surface. Such a reaction may be used to prepare a silica-supported titanium epoxidation catalyst. For example, in some embodiments, the resulting catalyst is less prone to leaching. The groups $R_1$, $R_2$, $R_3$, $R_4$, $R_5$ are each independently —H, —OH, —SH, —CN, —F, —CF$_3$, —NH$_2$, alkyl$_{(C \leq 8)}$, alkenyl$_{(C \leq 8)}$, alkynyl$_{(C \leq 8)}$, aryl$_{(C \leq 12)}$, aralkyl$_{(C \leq 12)}$, heteroaryl$_{(C \leq 8)}$, heterocycloalkyl$_{(C \leq 12)}$, alkoxy$_{(C \leq 8)}$, aryloxy$_{(C \leq 12)}$, acyloxy$_{(C \leq 8)}$, alkylamino$_{(C \leq 8)}$, dialkylamino$_{(C \leq 8)}$, alkenylamino$_{(C \leq 8)}$, arylamino$_{(C \leq 8)}$, aralkylamino$_{(C \leq 8)}$, alkylthio$_{(C \leq 8)}$, acylthio$_{(C \leq 8)}$, alkylsulfonylamino$_{(C \leq 8)}$, or substituted versions of any of these groups.
Figure 3:
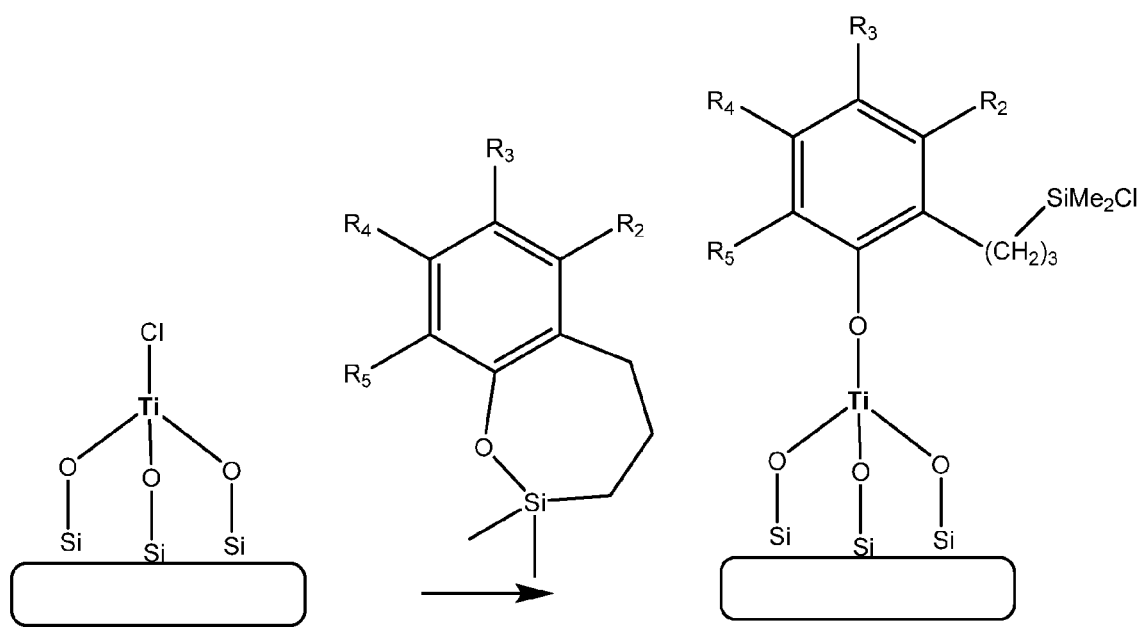
FIG. 3 shows an example of a reaction occurring between an optionally substituted tetrahydrobenzooxasilepine and Ti—Cl attached to a silica surface. Such a reaction may be used to prepare a silica-supported titanium epoxidation catalyst. For example, in some embodiments, the resulting catalyst is less prone to leaching. The groups $R_2$, $R_3$, $R_4$, and $R_5$ are each independently —H, —OH, —SH, —CN, —F, —CF$_3$, —NH$_2$, alkyl$_{(C \leq 8)}$, alkenyl$_{(C \leq 8)}$, alkynyl$_{(C \leq 8)}$, aryl$_{(C \leq 12)}$, aralkyl$_{(C \leq 12)}$, heteroaryl$_{(C \leq 8)}$, heterocycloalkyl$_{(C \leq 12)}$, alkoxy$_{(C \leq 8)}$, aryloxy$_{(C \leq 12)}$, acyloxy$_{(C \leq 8)}$, alkylamino$_{(C \leq 8)}$ dialkylamino$_{(C \leq 8)}$ alkenylamino$_{(C \leq 8)}$, arylamino$_{(C \leq 8)}$ aralkylamino$_{(C \leq 8)}$, alkylthio$_{(C \leq 8)}$ acylthio$_{(C \leq 8)}$, alkylsulfonylamino$_{(C \leq 8)}$, or substituted versions of any of these groups.
Figure 4:
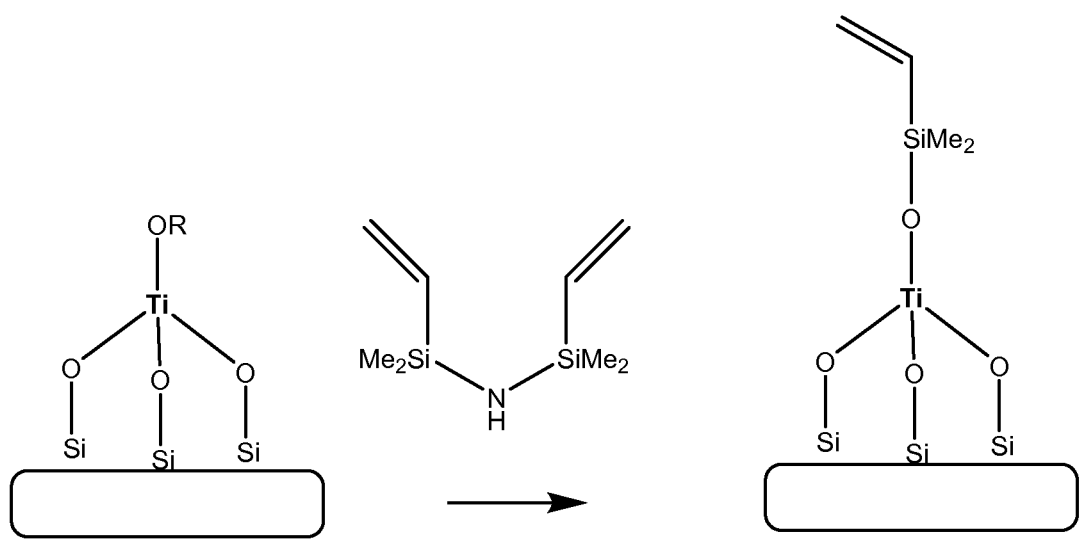
FIG. 4 shows an example of a reaction occurring between bis(dimethyl(vinyl)silyl)amine and Ti—OR attached to a silica surface. Such a reaction may be used to prepare a silica-supported titanium epoxidation catalyst. For example, in some embodiments, the resulting catalyst is less prone to leaching. The group R is —H, alkyl$_{(C\leq 8)}$, alkenyl$_{(C\leq 8)}$, aryl$_{(C\leq 12)}$, aralkyl$_{(C\leq 12)}$, heterocycloalkyl$_{(C\leq 12)}$, or substituted versions of any of these groups.

In general, epoxidation reactions may be represented by the following reaction scheme:

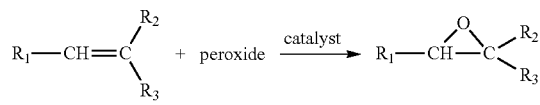

In epoxidation reactions, a mixture containing at least one olefin and a peroxide is contacted with a catalyst resulting in formation of the corresponding epoxide. In the above scheme, each of $R_1$, $R_2$, and $R_3$ are independently selected from hydrogen, alkyl, or substituted alkyl. When either of $R_1$, $R_2$, and $R_3$ are substituted, $R_1$, $R_2$, and $R_3$ contains one or more functional groups that are compatible with the peroxide and catalyst, such as hydroxyl or halide groups. In some embodiments, $R_1$, $R_2$, and $R_3$ are independently hydrogen or $C_1$-$C_{30}$ alkyl. In specific embodiments, $R_1$, $R_2$, and $R_3$ are independently hydrogen or $C_1$-$C_{10}$ alkyl.

Olefins suitable for use are well known and have at least one carbon-carbon double bond capable of epoxidation. Preferably, a $C_2$-$C_{60}$ olefin, more preferably a $C_3$-$C_{10}$ olefin, is used. Especially preferred olefins are acyclic $C_3$-$C_{10}$ olefins such as propylene, butene, pentene, hexene, heptene, octene, nonene, decene, and isomers thereof. Also preferred are olefins substituted with a hydroxyl or halogen such as allyl alcohol or allyl chloride.

Suitable organic peroxides are hydroperoxides that have the general structure R—OOH, where R is an aliphatic, cycloaliphatic, or aromatic radical, preferably with 3 to 50 carbons, more preferably 3 to 20 carbons. Preferred organic hydroperoxides are $C_3$-$C_{20}$ hydrocarbon hydroperoxides. Particularly preferred are $C_3$-$C_{15}$ secondary and tertiary hydroperoxides, for example, ethylbenzene hydroperoxide, tert-butylhydroperoxide, tert-amylhydroperoxide, cyclohexyl hydroperoxide, cumene hydroperoxide, and the like.

Hydrogen peroxide, an inorganic peroxide, is suitable for use in some olefin epoxidations as an alternative to organic hydroperoxides.

The olefin to peroxide or hydroperoxide molar ratio can vary, but it is preferable to use a molar ratio of from 1:1 to 20:1. A more preferred molar ratio of olefin to peroxide or hydroperoxide is 1.5:1 to 10:1.

The olefin to catalyst ratio can also vary. Generally, it is preferred to use the minimum concentration of catalyst effective to achieve a desirable epoxide yield and selectivity. In some embodiments, the catalyst to olefin ratio is within the range of 0.01 to 100 mmoles of titanium per mole of olefin; a more preferred range is from 0.1 to 10 mmoles of titanium per mole of olefin.

II. Catalysts

Catalysts useful for the present disclosure generally comprise titanium or niobium and a siliceous solid. In some embodiments, titanium is present in the catalyst in an amount (based upon the total weight of the catalyst) within the range of 0.5 to 10 wt. %, preferably 1 to 6 wt. %, more preferably 3 to 5 wt. %, based on the total weight of the catalyst.

In addition to titanium, the catalysts comprise a siliceous solid. In some embodiments, the siliceous solid is present in the catalyst in an amount (based upon the total weight of the catalyst) within the range of 90 to 99.5 wt. %, preferably 94 to 99 wt. %, most preferably 95 to 97 wt. %, based on the total weight of the catalyst.

Catalysts useful for the present disclosure comprise a siliceous solid. Inorganic siliceous solids suitable for use are generally well known. The solids contain a major proportion of silicon dioxide ($SiO_2$) and may be referred to herein generically as "silicas." Amorphous (i.e., non-crystalline) silicon oxides are preferred.

Suitable inorganic siliceous solids include synthetic porous silicas, silica powders, refractory oxides, mesoporous molecular sieves, essentially pure silica, and other siliceous solids.

Suitable synthetic porous silicas consist of particles of amorphous silica flocculated or linked together so that the particles form a relatively dense, close-packed mass. Representatives of such materials are silica gel and precipitated silica. These silica products have numerous pores, voids, or interstices throughout their structures.

Suitable silica powders may include synthetic silica powders consisting of particles of amorphous silica flocculated in open-packed, readily disintegrated, loosely knit aggregates. Illustrative silica powders include fumed, pyrogenic silicas obtained by the combustion of hydrogen and oxygen with silicon tetrachloride or silicon tetrafluoride.

Refractory oxides are also suitable for use. These synthetic inorganic oxide materials contain a major proportion of silica. Suitable refractory oxides include silica-aluminas, silica-magnesias, silica-zirconias, silica-alumina-borias, silica-alumina-magnesias, and the like.

Molecular sieves, particularly large pore or mesoporous molecular sieves such as MCM-41, MCM-48 and M41S, may also be utilized as the inorganic siliceous solid.

Particularly preferred synthetic inorganic siliceous solids comprise essentially pure silica. "Essentially pure" silica as defined herein is at least 97 wt. % silica. Preferred essentially pure silicas may contain at least 98 wt. % silica, preferably at least 99 wt. % silica. Many silicas are commercially available and sold for various purposes, such as thin layer chromatography, column chromatography, catalyst supports, and other uses. Suitable silicas include, for example, Davisil® silica gels such as Davisil® 643 (products of Grace Davison) and microspherical silica gels produced by PQ Corporation in the "MS-" series, including MS-3050 silica, a grade commonly used to support polyolefin catalysts.

Other siliceous inorganic solids include naturally occurring mineral silicates such as hydrous magnesium silicates, and clay minerals such as hectorites, kaolins, bentonites, and the like.

Preferred siliceous solids have high surface areas, particularly at least 25 m$^2$/g, preferably at least 200 m$^2$/g, more preferably at least 400 m$^2$/g, and most preferably at least 500 m$^2$/g. A preferred range is from 25 to 1000 m$^2$/g, more preferably from 200 to 1000 m$^2$/g.

In some embodiments, the physical form of catalyst includes, but is not limited to, powder, flakes, granules, spheres, or pellets. The inorganic siliceous solid may be in such form prior to impregnation and calcination or, alternatively, be converted after impregnation and/or calcination from one form to a different physical form by conventional techniques such as extrusion, pelletization, grinding, or the like.

In some embodiments, the catalyst may be reacted with a silylating agent. Generally, the amount of silylating agent used is an amount effective to reduce the concentration of surface hydroxyl groups on the siliceous solid and convert at least some of those groups to silyl ethers. In some embodiments, the amount of silylating agent used will be within the range of 10 to 70 wt. %, preferably 20 to 50 wt. %, based on the total amount of catalyst. In other embodiments, the amount of silylating agent used will be within the range of 0.2 to 2 moles, preferably 0.5 to 1.5 moles, per mole of free hydroxyl groups present in the siliceous solid.

Suitable silylating agents are silicon compounds capable of reaction with one or more hydroxyl groups of a composition, usually a siliceous solid, to form at least one silicon-oxygen single bond. Suitable silylating agents include, for example, organosilanes, organosilylamines and organosilazanes. Suitable organosilanes include, for example, chlorotrimethylsilane, dichlorodimethylsilane, chlorotriethylsilane, chlorodimethylphenylsilane, and the like. Preferred silylating agents include tetra-substituted silanes having from 1 to 3 halo substituents selected from chlorine, bromine, and iodine with the remainder of the substituents being methyl, ethyl or a combination thereof. Suitable organodisilazanes may have the formula: $R_3Si$—NH—Si—$R_3$, wherein each R is independently a alkyl group (preferably, $C_1$-$C_4$ alkyl) or hydrogen. Especially preferred are hexaalkyl-substituted disilazanes such as, for example, hexamethyidisilazane.

In one aspect, the present disclosure relates to a method of preparing a catalyst. In some embodiments, the catalyst may be used for an olefin epoxidation reaction. In some embodiments, the method for making the catalyst includes three steps. In a first step, an inorganic siliceous solid is added to a column to produce a solid-filled column. In a second step, a solution comprising a metal complex and a hydrocarbon solvent is added to the solid-filled column to produce a metal-complex-impregnated solid. In a third step, the metal-complex-impregnated solid is calcined to produce the catalyst.

In embodiments of the present disclosure, an inorganic siliceous solid is added to a column. Suitable columns include, but are not limited to columns that may be used for chromatography. Although the column may be made of a variety of materials, the column should be acid-resistant because HCl is generated, in situ, when the siliceous solid is contacted with the titanium tetrachloride solution. Additionally, the column should be temperature resistant due to high calcination temperatures. For example, quartz columns are preferred for small-scale laboratory preparations.

The addition can be done in any desired manner, and the amount of siliceous solid used can vary. In some embodiments, it is possible to fill only a minor proportion of the column, or most of it, as the circumstances may suggest. For instance, the column may be filled with siliceous solid to a column height that exceeds the inside diameter of the column, although this need not be the case. It may be desirable, in some cases, to use a filter funnel or similar device as a substitute for the column, in which case, the diameter of the silica column will often exceed its height.

Upon addition of the siliceous solid to the column, a solid-filled column is produced.

The inorganic siliceous solid may be dried, if desired, before or after it is added to the column. Drying may be accomplished, for example, by heating the inorganic siliceous solid for several hours at a temperature from 100° C. to 700° C., preferably 200° C. to 600° C. Vacuum or a flowing stream of a dry gas such as nitrogen may be applied to accelerate drying.

The present disclosure provides processes for forming epoxides. In some embodiments, the processes comprise contacting a solution of an olefin, preferably propylene, and a peroxide with a catalyst to produce the epoxide. The catalyst, which has already been discussed in detail above, is made by a method comprising adding an inorganic siliceous solid to a column to produce a solid-filled column, adding to the solid-filled column a solution comprising metal and a hydrocarbon solvent to produce a metal-complex-impregnated solid, and calcining the metal-complex-impregnated solid at a temperature from 200° C. to 400° C. to produce the catalyst. The inorganic siliceous solid has a pore volume of at least 0.8 $cm^3$/g.

Generally, epoxidation is conducted in the liquid phase in solvents or diluents that are liquid at the reaction temperature and pressure and are substantially inert to the reactants and the products produced therefrom. In commercial practice, it is generally most economical to use as a solvent the hydrocarbon or alcohol used to produce the organic hydroperoxide reactant. For example, when tert-butylhydroperoxide is utilized, tert-butyl alcohol is preferred as the epoxidation solvent.

In some embodiments, the peroxide is selected from the group consisting of hydrogen peroxide and organic hydroperoxides. Preferably, the organic hydroperoxide is selected from the group consisting of tert-butylhydroperoxide and ethylbenzene hydroperoxide. The organic hydroperoxide may be present at concentrations of from about 1 to 50 wt. % of the epoxidation reaction mixture (including olefin).

Epoxidation may be conducted at moderate temperatures and pressures. Suitable reaction temperatures vary from 0° C. to 200° C., but preferably from 25° C. to 150° C. The reaction is preferably conducted at or above atmospheric pressure. The pressure may vary from 1 atmosphere to 100 atmospheres. The reaction mixture may, for example, be maintained substantially in a non-gaseous phase or as a two-phase (gas/liquid) system. The catalyst, of course, is heterogeneous and thus is present as a solid phase during the epoxidation process.

Suitable reactor configurations for epoxidation include, but are not limited to continuous, batch, or semi-continuous procedures. When the epoxidation has proceeded to the desired extent, the product mixture is separated and the products (epoxide and the alcohol derived from the organic hydroperoxide) are recovered by conventional methods such as fractional distillation, selective extraction, filtration, and the like. The reaction solvent, the catalyst composition, and any unreacted olefin or organic hydroperoxide may be recycled and reused.

The epoxidation reaction provides an epoxide product in accord with the following reaction scheme:

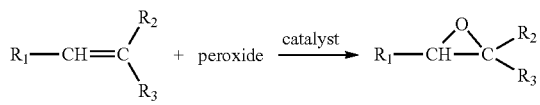

Suitable epoxide products have the formula shown above in which each of $R_1$, $R_2$, and $R_3$ is independently hydrogen, alkyl, or alkyl substituted with one or more functional groups that are compatible with the peroxide and catalyst, such as hydroxyl or halide groups. In some embodiments, $R_1$, $R_2$, and $R_3$ are independently hydrogen or $C_1$-$C_{30}$ alkyl. In specific embodiments, $R_1$, $R_2$, and $R_3$ are independently hydrogen or $C_1$-$C_{10}$ alkyl.

The epoxide may derive from epoxidation of a $C_2$-$C_{60}$ olefin, more preferably a $C_3$-$C_{10}$ olefin. Especially preferred epoxides result from epoxidation of acyclic $C_3$-$C_{10}$ olefins to give epoxides such as propylene oxide, 1,2-butene oxide, isobutylene oxide, pentene oxides, hexene oxides, heptane oxides, octane oxides, nonene oxides, decene oxides, and the like. Also preferred are epoxides substituted with a hydroxyl or halogen such as glycidol and epichlorohydrin. Propylene oxide is most preferred.

In some embodiments, the peroxide conversion is at least 50%, preferably at least 60%, more preferably at least 70%, and most preferably at least 80%. A preferred range is 50 to 99%, preferably 60 to 99%, more preferably 70 to 99%. As shown in the examples below, peroxide conversion improves when the column preparation method of the present disclosure is used. The term "peroxide conversion," as used herein refers to the percentage of inorganic peroxide or organic hydroperoxide that is converted to water or an alcohol, respectively. Thus, for example, when TBHP is the peroxide, the percentage of TBHP molecules converted to tert-butyl alcohol is the "peroxide conversion."

In some embodiments, the peroxide selectivity is greater than 95%, preferably greater than 97%, more preferably greater than 98%. As shown in the examples below, peroxide selectivity improves when the column preparation method of the present disclosure is used. The term "peroxide selectivity," as used herein refers to the percentage of inorganic peroxide or organic hydroperoxide for which the active oxygen from the peroxide is incorporated into an epoxide product. Thus, for example, when TBHP is the peroxide, and propylene is the olefin, the percentage of active oxygens from the converted TBHP molecules that become incorporated into a propylene oxide molecule is the "peroxide selectivity."

III. Process Scale-Up

The above methods can be further modified and optimized for preparative, pilot- or large-scale production, either batch or continuous, using the principles and techniques of process chemistry as applied by a person skilled in the art. Such principles and techniques are taught, for example, in *Practical Process Research & Development* (2012), which is incorporated by reference herein.

IV. Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "====" represents a single bond or a double bond. Thus, for example, the formula

includes

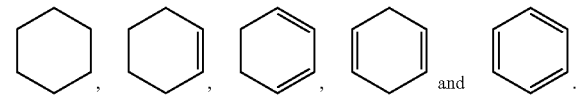

And it is understood that no one such ring atom forms part of more than one double bond. Furthermore, it is noted that the covalent bond symbol "—", when connecting one or two stereogenic atoms, does not indicate any preferred stereochemistry. Instead, it cover all stereoisomers as well as mixtures thereof. The symbol "〜〜", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◀" means a single bond where the group attached to the thick end of the wedge is "out of the page." The symbol "▮▮▮" means a single bond where the group attached to the thick end of the wedge is "into the page". The symbol "〜〜" means a single bond where the geometry around a double bond (e.g., either E or Z) is undefined. Both options, as well as combinations thereof are therefore intended. The bond orders described above are not limiting when one of the atoms connected by the bond is a metal atom (M). In such cases, it is understood that the actual bonding may comprise significant multiple bonding and/or ionic character. Therefore, unless indicated otherwise, the formulas M-C, M=C, M----C, and M====C, each refers to a bond of any and type and order between a metal atom and a carbon atom. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

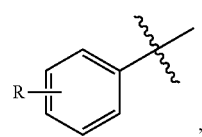

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

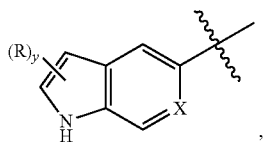

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms. (Cn-n') defines both the minimum (n) and maximum number (n') of carbon atoms in the group. Similarly, "alkyl$_{(C2-10)}$" designates those alkyl groups having from 2 to 10 carbon atoms.

The term "saturated" as used herein means the compound or group so modified has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl).

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl, with the carbon atom that forms the point of attachment also being a member of one or more non-aromatic ring structures wherein the cycloalkyl group consists of no atoms other than carbon and hydrogen. As used herein, the term does not preclude the presence of one or more alkyl groups (carbon number limitation permitting) attached to the ring or ring system. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

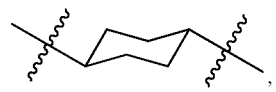 [SMILES: *C1CCC(*)CC1]

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —S(O)$_2$NH$_2$, —SiH$_2$Cl, or —Si(CH$_3$)$_2$Cl. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting example of a haloalkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups.

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include:

—CH=CH₂ (vinyl), —CH=CHCH₃, —CH=CHCH₂CH₃, —CH₂CH=CH₂ (allyl), —CH₂CH=CHCH₃, and —CH=CHCH=CH₂. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH₃)CH₂—, —CH=CHCH₂—, and

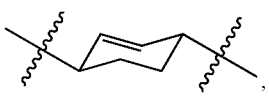 [SMILES: *C1C=CC(*)CC1]

are non-limiting examples of alkenediyl groups. It is noted that while the alkenediyl group is aliphatic, once connected at both ends, this group is not precluded from forming part of an aromatic structure. The terms "alkene" or "olefin" are synonymous and refer to a compound having the formula H—R, wherein R is alkenyl as this term is defined above. A "terminal alkene" refers to an alkene having just one carbon-carbon double bond, wherein that bond forms a vinyl group at one end of the molecule. When any of these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, —S(O)₂NH₂, —SiH₂Cl, or —Si(CH₃)₂Cl. The groups, —CH=CHF, —CH=CHCl and —CH=CHBr, are non-limiting examples of substituted alkenyl groups.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH₃, and —CH₂C≡CCH₃, are non-limiting examples of alkynyl groups. An "alkyne" refers to the compound H—R, wherein R is alkynyl. When any of these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, —S(O)₂NH₂, —SiH₂Cl, or —Si(CH₃)₂Cl.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C₆H₄CH₂CH₃ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

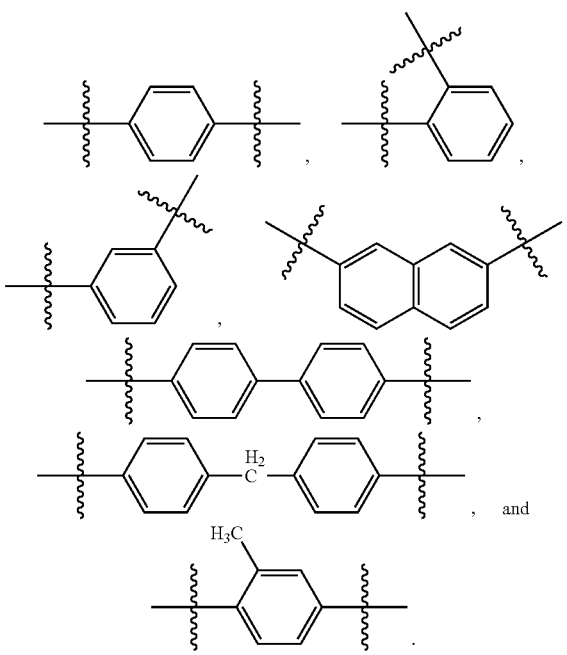

An "arene" refers to the compound H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, —S(O)₂NH₂, —SiH₂Cl, or —Si(CH₃)₂Cl.

The term "aralkyl" when used without the "substituted" modifier refers to the monovalent group-alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, —S(O)₂NH₂, —SiH₂Cl, or —Si(CH₃)₂Cl. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolinyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl, aryl, and/or aralkyl groups (carbon number limitation permitting) attached to the aromatic ring or aromatic ring system. Non-limiting examples of heteroarenediyl groups include:

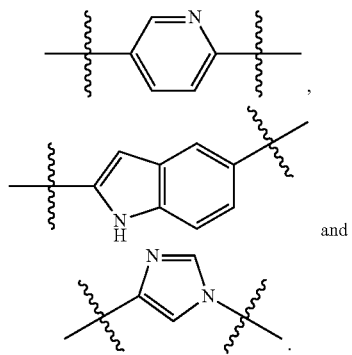

A "heteroarene" refers to the compound H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —S(O)$_2$NH$_2$, —SiH$_2$Cl, or —Si(CH$_3$)$_2$Cl.

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, C(O)CH(CH$_3$)$_2$, C(O)CH(CH$_2$)$_2$, C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —S(O)$_2$NH$_2$, —SiH$_2$Cl, or —Si(CH$_3$)$_2$Cl. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$ (methoxy), —OCH$_2$CH$_3$ (ethoxy), —OCH$_2$CH$_2$CH$_3$, —OCH(CH$_3$)$_2$ (isopropoxy), —OC(CH$_3$)$_3$ (tert-butoxy), —OCH(CH$_2$)$_2$, —O-cyclopentyl, and —O-cyclohexyl. The terms "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is alkenyl, alkynyl, aryl, aralkyl, heteroaryl, heterocycloalkyl, and acyl, respectively. The term "alkoxydiyl" refers to the divalent group —O-alkanediyl-, —O-alkanediyl-O—, or -alkanediyl-O-alkanediyl-. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —S(O)$_2$NH$_2$, —SiH$_2$Cl, or —Si(CH$_3$)$_2$Cl.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", "heterocycloalkylamino" and "alkylsulfonylamino" when used without the "substituted" modifier, refers to groups, defined as —NHR, in which R is alkoxy, alkenyl, alkynyl, aryl, aralkyl, heteroaryl, heterocycloalkyl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH— alkanediyl-, —NH— alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —S(O)$_2$NH$_2$, —SiH$_2$Cl, or —Si(CH$_3$)$_2$Cl. The groups —NHC(O)OCH$_3$ and —NHC(O)NHCH$_3$ are non-limiting examples of substituted amido groups.

The term "alkylsilyl" when used without the "substituted" modifier refers to a monovalent group, defined as —SiH$_2$R, —SiHRR', or —SiRR'R", in which R, R' and R" can be the same or different alkyl groups, or any combination of two of R, R' and R" can be taken together to represent an alkanediyl. The groups, —SiH$_2$CH$_3$, —SiH(CH$_3$)$_2$, —Si(CH$_3$)$_3$ and —Si(CH$_3$)$_2$C(CH$_3$)$_3$, are non-limiting examples of unsubstituted alkylsilyl groups. The term "substituted alkylsilyl" refers to —SiH$_2$R, —SiHRR', or —SiRR'R", in which at least one of R, R' and R" is a substituted alkyl, two of R, R' and R" can be taken together to represent a substituted alkanediyl. When more than one of R, R' and R" is a substituted alkyl, they can be the same of different. Any of R, R' and R" that are not either substituted alkyl or substituted alkanediyl, can be either alkyl, either the same or different, or can be taken together to represent a alkanediyl with two or more saturated carbon atoms, at least two of which are attached to the silicon atom.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

As used herein, average molecular weight refers to the weight average molecular weight (Mw) as determined by static light scattering.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

An "isomer" of a first compound is a separate compound in which each molecule contains the same constituent atoms as the first compound, but where the configuration of those atoms in three dimensions differs.

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

V. Examples

The following examples are included to demonstrate preferred embodiments of the disclosure. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

A. Synthesis and Characterization of Catalyst Precursor Complexes

EXAMPLE 1

Methylenebis(6-tert-butyl-4-methylphenoxy-2-yl) dichlorotitanium (IV)

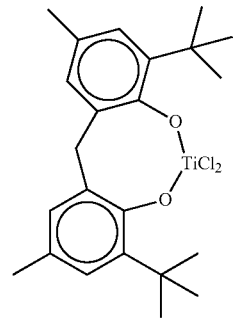

The synthesis of this complex was based on the procedure in *Inorg. Chem.*, 1991, 30, 145-148, which is incorporated herein by reference in its entirety. TiCl$_4$ (1.90 g, 10 mmol) was added to cooled (−40° C.) suspension of commercially available bisphenol (3.41 g, 10 mmol) in hexane (50 mL). The reaction mixture was allowed to warm to room temperature and stirred for 16 h. Red precipitate was filtered off and dried in vacuo. The yield was 3.15 g (69%), orange crystalline powder.

$^1$H NMR (CDCl$_3$) δ: 1.44 (s, 18H); 2.32 (s, 6H); 3.68 (d, $^2$J=14.7 Hz, 1H); 4.09 (d, $^2$J=14.7 Hz, 1H); 6.97 (bs, 2H); 7.15 (bs, 2H)

EXAMPLE 2

Tri(2-hydroxy-3-tert-butyl-5-methylphenyl)methane

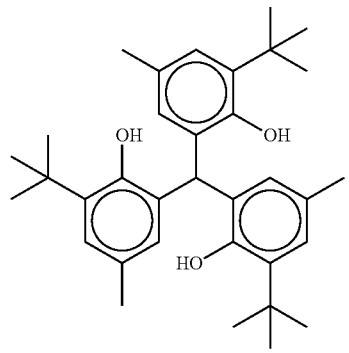

HC(OEt)₃ (14.82 g, 100 mmol) was added to cooled (0° C.) magnesium phenolate, prepared by reaction of 2-tert-butyl-4-methylphenol (52.6 g, 320 mmol) and 350 mmol of EtMgBr solution. Reaction mixture was allowed to warm to room temperature, toluene (200 mL) was added, the mixture was heated (glycol external bath, 120° C., ether was distilled off) and refluxed for 8 h. After cooling, the mixture was treated by 5% HCl, and extracted by $CH_2Cl_2$. Combined organic phase was dried over $MgSO_4$, evaporated, the residue was recrystallized from MeOH. The yield of white crystalline product was 14.6 g (29%).

$^1$H NMR (CDCl₃) δ: 1.37 (s, 27H); 2.19 (s, 9H); 4.80 (s, 3H, —OH); 5.58 (s, 1H); 6.55 (bs, 3H); 7.09 (bs, 3H).

EXAMPLE 3

Tri(2-hydroxy-3-tert-butyl-5-methylphenyl)methane, dichlorotitanium (IV) complex

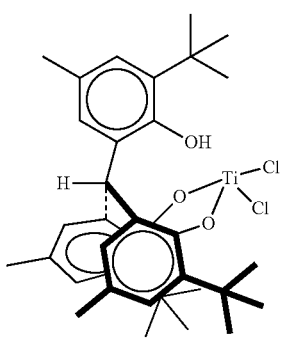

TiCl₄ (0.95 g, 5 mmol) was added to cooled (−40° C.) suspension of tri(2-hydroxy-3-tert-butyl-5-methylphenyl)methane (2.51 g, 5 mmol) in hexane (50 mL). The reaction mixture was allowed to warm to room temperature, stirred for 16 h, 30 mL of hexane was distilled off under reduced pressure, red precipitate was filtered off and dried in vacuo. The yield was 2.20 g (71%), red-violet crystalline powder.

Reaction in $CH_2Cl_2$ yielded the same result (bis-phenolate).

$^1$H NMR (CDCl₃) δ: 1.33 (s, 9H); 1.46 (s, 18H); 2.24 (s, 3H); 2.29 (s, 6H); 4.34 (s, 1H); 5.52 (s, 1H); 6.91 (bs, 1H); 7.04-7.07 (m, 5H).

$^{13}$C NMR (CDCl₃) δ: 21.34; 21.42; 29.88; 30.33; 34.59; 35.24; 41.77; 77.00; 126.50; 126.87; 127.46; 127.70; 128.29; 134.62; 136.12; 136.50; 137.69; 151.10; 163.39

EXAMPLE 4

Tri(2-hydroxy-3-tert-butyl-5-methylphenyl)methane, chlorotitanium (IV) complex

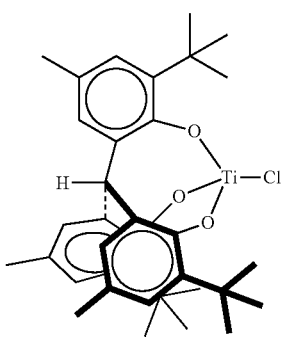

BuLi (1.6M in hexane, 10 mL, 16 mmol) was added at −20° C. to solution of tri(2-hydroxy-3-tert-butyl-5-methylphenyl)methane (2.51 g, 5 mmol) in ether (100 mL). The mixture was allowed to warm to room temperature (crystalline precipitate formed), cooled to −40° C., and TiCl₄ (0.95 g, 5 mmol) was added. The reaction mixture was allowed to warm to room temperature, stirred for 16 h, $CH_2Cl_2$ (100 mL) was added, and the mixture was filtered. Filtrate was evaporated under reduced pressure, the residue was washed by pentane and dried in vacuo. The yield was 2.11 g (73%), orange crystalline powder.

$^1$H NMR (CDCl₃) δ: 1.16; 1.32; 1.37; 1.39 {27H}; 2.19; 2.20; 2.26 {9H}; 4.76; 4.79 {1H}; 5.92; 6.55; 6.79; 6.90; 6.98; 7.04; 7.08; 7.19 {6H}.

EXAMPLE 5

Methylenebis(6-tert-butyl-4-methylphenoxy-2-yl) diisopropoxytitanium (IV)

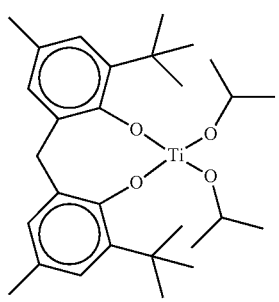

Titanium isopropoxide (2.84 g, 10 mmol) was added to cooled (−20° C.) suspension of commercially available bisphenol (3.41 g, 10 mmol) in pentane (50 mL). The reaction mixture was allowed to warm to room temperature and stirred for 16 h (orange-brown solution). The mixture was evaporated (residual volume 15 mL). The precipitate was filtered off and dried in vacuo. The yield was 4.05 g (80%), orange crystalline powder.

$^1$H NMR (CDCl₃) δ: 1.33 (d, 12H); 1.39 (s, 18H); 2.25 (s, 6H); 3.48 (d, $^2J$=13.7 Hz, 1H); 4.29 $^2J$=13.7 Hz, 1H); 4.73 (m, 2H); 6.88 (bs, 2H); 7.05 (bs, 2H).

$^{13}$C NMR (CDCl₃) δ: 21.01; 26.49; 30.00; 33.88; 34.90; 79.24; 125.46; 128.48; 129.82; 133.35; 136.35; 159.56.

EXAMPLE 6

Bis(2,6-di-tert-butyl-4-methylphenoxy) dichlorotitanium (IV)

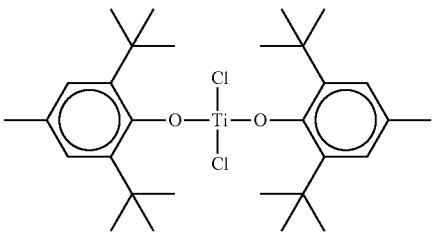

BuLi (1.6M in hexane, 10 mL, 16 mmol) was added at −20° C. to solution of ionol (3.52 g, 16 mmol) in hexane (50 mL). The mixture was allowed to warm to room temperature (crystalline precipitate formed), cooled to −40° C., and TiCl₄ (1.52 g, 8 mmol) was added. The reaction mixture was allowed to warm to room temperature and stirred for 16 h.

The mixture was filtered, the precipitate was washed by $CH_2Cl_2$, combined filtrate was concentrated under reduced pressure to residual volume ~15 mL, precipitate was filtered off and dried in vacuo. The yield was 3.44 g (77%), red-violet crystalline powder.

$^1$H NMR (CDCl$_3$) δ: 1.49 (s, 36H); 2.29 (s, 6H); 7.01 (s, 4H).

$^{13}$C NMR (CDCl$_3$) δ: 21.46; 31.79; 35.40; 125.87; 133.41; 140.11; 169.40.

EXAMPLE 7

Bis(2,6-diisopropylphenoxy) trichloroniobium (IV)

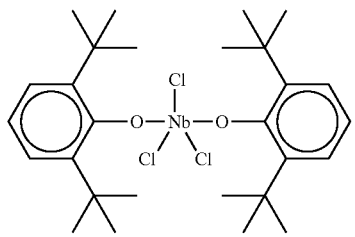

NbCl$_5$ (2.70 g, 10 mmol) was added to cooled (−40° C.) solution of 2,6-diisopropylphenol (3.57 g, 10 mmol) in benzene (25 mL). The reaction mixture was allowed to warm to room temperature and stirred for 16 h. Benzene was evaporated under reduced pressure, hexane (25 mL) was added, precipitate was filtered off and dried in vacuo. The yield was 4.01 g (72%), red crystalline powder.

$^1$H NMR (CDCl$_3$) δ: 1.16 (d, 24H); 3.75 (m, 4H); 7.11 (m, 6H).

$^{13}$C NMR (CDCl$_3$) δ: 24.34; 27.03; 123.96; 127.07; 128.33; 141.24.

EXAMPLE 8

Methylenebis(6-tert-butyl-4-methylphenoxy-2-yl) trichloroniobium (V)

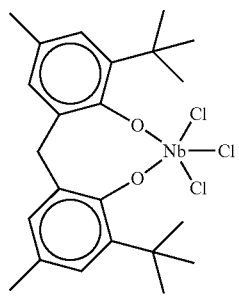

NbCl$_5$ (2.70 g, 10 mmol) was added to cooled (−40° C.) suspension of commercially available bisphenol (3.41 g, 10 mmol) in benzene (25 mL). The reaction mixture was allowed to warm to room temperature and stirred for 16 h. Hexane (25 mL) was added, red precipitate was filtered off and dried in vacuo. The yield was 4.15 g (77%), red-violet crystalline powder.

$^1$H NMR (CDCl$_3$) δ: 1.45 (s, 18H); 2.32 (s, 6H); 3.64 (d, $^2$J=14.7 Hz, 1H); 4.48 (bd, $^2$J=14.7 Hz, 1H); 7.03 (bs, 2H); 7.09 (bs, 2H)

$^{13}$C NMR (CDCl$_3$) δ: 21.24; 30.78; 35.18; 126.42; 128.33; 128.68; 128.88; 135.55; 139.94.

EXAMPLE 9

Bis(2,6-dimethylphenoxy) trichloroniobium (V)

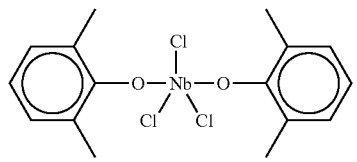

NbCl$_5$ (2.70 g, 10 mmol) was added to cooled (−40° C.) solution of 2,6-dimethylphenol (2.57 g, 21 mmol) in benzene (25 mL). The reaction mixture was allowed to warm to room temperature and stirred for 16 h. Hexane (25 mL) was added, precipitate was filtered off and dried in vacuo. The yield was 3.22 g (73%), red-violet crystalline powder.

$^1$H NMR (CDCl$_3$) δ: 2.54 (s, 12H); 6.92-6.99 (m, 6H).

$^{13}$C NMR (CDCl$_3$) δ: 17.49; 126.73; 128.65; 128.83; 131.05.

EXAMPLE 10

Tris(2,6-diisopropylphenoxy) dichloroniobium (V)

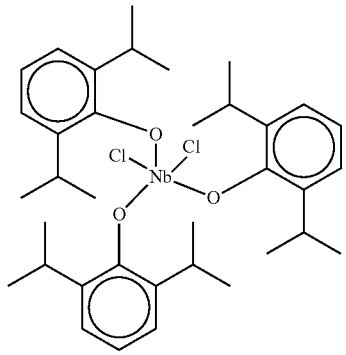

NbCl$_5$ (2.70 g, 10 mmol) was added to cooled (−40° C.) solution of 2,6-diisopropylphenol (6.24 g, 35 mmol) in benzene (35 mL). The reaction mixture was stirred at 80° C. for 6 h, cooled, and stirred for 16 h. Benzene was evaporated under reduced pressure (residual volume 15 mL), hexane (50 mL) was added, precipitate was filtered off and dried in vacuo. The yield was 4.78 g (69%), orange crystalline powder.

$^1$H NMR (CDCl$_3$) δ: 1.20 (d, 36H); 3.36 (m, 6H); 7.05-7.16 (m, 9H).

$^{13}$C NMR (CDCl$_3$) δ: 23.72; 27.99; 123.59; 125.22; 138.80; 159.56.

EXAMPLE 11

Bis(2,6-dimethylphenoxy) dichlorotitanium (IV)

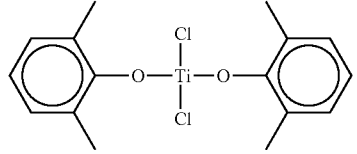

TiCl$_4$ (1.90 g, 10 mmol) was added to cooled (−0° C.) solution of 2,6-dimethylphenol (2.57 g, 21 mmol) in hexane (25 mL). The reaction mixture was allowed to warm to room temperature and stirred for 16 h. Hexane was evaporated, pentane (20 mL) was added, crystallization at −20° C. leads to the product (red crystalline powder). The yield was 2.89 g (80%).

$^1$H NMR (CDCl$_3$) δ: 2.34 (s, 12H); 6.96 (m, 6H).

$^{13}$C NMR (CDCl$_3$) δ: 16.89; 124.61; 127.75; 128.30.

EXAMPLE 12

Bis(2,6-diisopropylphenoxy) dichlorotitanium (IV)

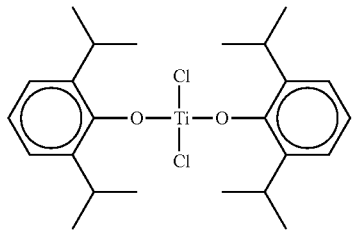

TiCl$_4$ (1.90 g, 10 mmol) was added to cooled (−0° C.) solution of 2,6-diisopropylphenol (3.74 g, 21 mmol) in hexane (30 mL). The reaction mixture was allowed to warm to room temperature and stirred for 16 h. Hexane was evaporated, pentane (20 mL) was added, crystallization at −20° C. leads to the product (red crystalline powder). The yield was 2.98 g (63%).

$^1$H NMR (CDCl$_3$) δ: 1.19 (d, 24H); 3.42 (m, 4H); 7.06 (m, 6H).

$^{13}$C NMR (CDCl$_3$) δ: 23.14; 27.55; 123.19; 125.23; 138.08; 165.62.

EXAMPLE 13

Tris(2,6-dimethylphenoxy) dichloroniobium (V)

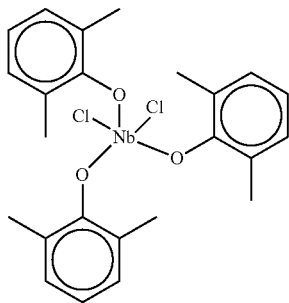

NbCl$_5$ (2.70 g, 10 mmol) was added to cooled (−40° C.) solution of 2,6-dimethylphenol (4.28 g, 35 mmol) in benzene (35 mL). The reaction mixture was stirred at 80° C. for 6 h, cooled, and stirred for 16 h. Toluene (10 mL) was added, the mixture was heated (solubilization), hot solution was separated by decantation, evaporated, pentane (25 mL) was added, precipitate was filtered off and dried in vacuo. The yield was 3.44 g (65%), orange crystalline powder.

$^1$H NMR (CDCl$_3$) δ: 2.25 (s); 2.33 (s); 2.39 (s); 2.40 (s) {18H}; 6.76-7.00 (mm, 9H).

$^{13}$C NMR (CDCl$_3$) δ: 15.84; 17.08; 17.55; 124.83; 128.57; 129.68.

EXAMPLE 14

Chloro(3-chloropropyl)dimethylsilane

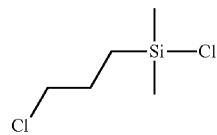

Solution of H$_2$PtCl$_6$ (100 mg) in THF (5 mL) was added dropwise within 15 min to heated (40° C.) and well stirred solution of allyl chloride (15.3 g, 200 mmol) and SiHMeCl$_2$ (20.8 g, 220 mmol) in THF (40 mL). The resulting mixture was distilled at 70 Torr., collecting fraction with B. p. 92-97° C. The yield was 21.2 g (62%).

$^1$H NMR (CDCl$_3$) δ: 0.42 (s, 6H); 0.93 (m, 2H); 1.87 (m, 2H); 3.53 (t, 2H).

$^{13}$C NMR (CDCl$_3$) δ: 1.55; 16.46; 26.56; 47.23.

EXAMPLE 15

(3-Chloropropyl)(2,4-cyclopentadien-1-yl)dimethylsilane

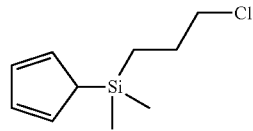

Chloro(3-chloropropyl)dimethylsilane (12.7 g, 74 mmol) was added to cooled to −40° C. suspension of CpLi (77 mmol) in Et$_2$O (70 mL) and THF (5 mL) in the presence of CuCN (50 mg). The mixture was allowed to warm to room temperature, stirred for 16 h, filtered, evaporated and distilled under reduced pressure, collecting fraction with B.p. 74-76° C./3 Torr. The yield was 12.25 g (82%).

For main isomer:

$^1$H NMR (CDCl$_3$) δ: −0.04 (s, 6H); 0.60 (m, 2H); 1.76 (m, 2H); 3.03 (bs, 1H); 3.48 (t, 2H); 6.45-6.65 (broad, 4H).

$^{13}$C NMR (CDCl$_3$) δ: −4.00; 12.85; 27.75; 47.71; 130.43; 132.86; 138.01.

EXAMPLE 16

1,1-Dimethyl-2,3,4,7a-tetrahydro-1H-cyclopenta[b]siline

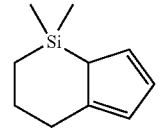

BuLi (1.6M in hexane, 34 mL, 54 mmol) was added to cooled to −40° C. solution of (3-chloropropyl)(2,4-cyclopentadien-1-yl)dimethylsilane (10.43 g, 51.9 mmol) in THF (40 mL). The mixture was allowed to warm to room temperature, refluxed for 6 h, stirred at room temperature for 16 h. Water (10 mL) and pentane (50 mL) were added, organic phase was separated, dried over MgSO$_4$, evaporated and distilled under reduced pressure, B.p. 69-72° C./8 Torr. The yield was 5.96 g (70%).

For main isomer:

$^1$H NMR (CDCl$_3$) δ: −0.60 (s, 3H); 0.31 (s, 3H); 0.67 (m, 2H); 1.31 (m, 2H); 2.14 (m, 2H); 3.16 (bs, 1H); 6.23 (bs, 1H); 6.39 (bs, 1H); 6.53 (bs, 1H).

$^{13}$C NMR (CDCl$_3$) δ: −9.69; −0.80; 13.10; 26.31; 31.07; 53.33; 123.64; 129.96; 130.71; 146.96.

EXAMPLE 17

η$^5$-[3-(Chlorodimethylsilyl)propyl]cyclopentadienyl trichlorotitanium (IV)

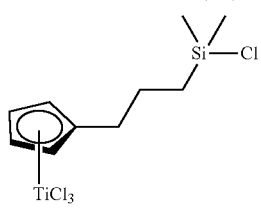

TiCl$_4$ (2.47 g, 13 mmol) in hexane (15 mL) was added to cooled (−40° C.) solution of 1,1-dimethyl-2,3,4,7a-tetrahydro-1H-cyclopenta[b]siline (2.28 g, 13.9 mmol) in toluene (20 mL). The mixture was allowed to warm to room temperature, stirred for 16 h, solvent was removed under reduced pressure, and the residue was recrystallized from hexane yielding 2.89 g (63%) of the product as green-brown crystalline powder.

$^1$H NMR (CDCl$_3$) δ: 0.43 (s, 6H); 0.90 (m, 2H); 1.80 (m, 2H); 2.92 (t, 2H); 6.86 (t, $^3$J=2.5 Hz, 2H); 6.95 (t, $^3$J=2.5 Hz, 2H).

$^{13}$C NMR (CDCl$_3$) δ: 1.58; 18.73; 23.84; 34.82; 123.15; 123.61; 144.23.

EXAMPLE 18

(2-Allylphenoxy)(dimethyl)silane

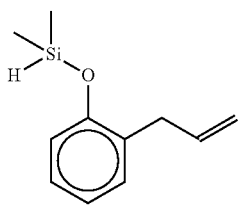

SiHMe$_2$Cl (15.1 g, 160 mmol) was added to cooled (0° C.) solution of 2-allylphenol (20.13 g, 150 mmol) and Et$_3$N (15.7 g, 155 mmol) in hexane (200 ml). The mixture was allowed to warm to room temperature, stirred for 20 min, filtered, solvent was removed under reduced pressure, and the residue was distilled (B. p. 88-89° C./6 Torr). The yield was 18.6 g (65%).

$^1$H NMR (CDCl$_3$) δ: 0.35 (d, 6H); 3.34 (d, 2H); 4.97 (m, 1H); 5.02 (s, 1H); 5.06 (m, 1H); 5.94 (m, 1H); 6.84 (d, 1H); 6.92 (t, 1H); 7.13 (m, 2H).

$^{13}$C NMR (CDCl$_3$) δ: −1.28; 34.50; 115.44; 118.11; 121.58; 127.23; 130.16; 130.58; 136.92; 153.37.

EXAMPLE 19

2,2-Dimethyl-2,3,4,5-tetrahydro-1,2-benzoxasilepine and 2,2,3-trimethyl-3,4-dihydro-2H-1,2-benzoxasiline

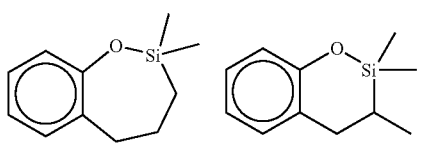

(2-Allylphenoxy)(dimethyl)silane (18.6 g, 97 mmol) was dissolved in toluene (30 mL), and Pt catalyst (0.2% mol) was added. The mixture was stirred for 10 min, and distilled yielding the product as a mixture of isomers. The yield was 15.5 g (83%). B.p. 82-86° C./6 Torr.

$^1$H NMR (CDCl$_3$) δ 0.19 (s, 6H); 0.78 (m, 2H); 1.84 (m, 2H); 2.72 (m, 2H); 6.87 (m, 2H); 7.07 (m, 2H).

$^{13}$C NMR (CDCl$_3$) δ: −1.42; 15.95; 23.02; 33.30; 120.70; 121.95; 127.50; 130.50; 133.37; 154.30.

EXAMPLE 20

2-{3-[Chloro(dimethyl)silyl]propyl}phenoxy trichlorotitanium

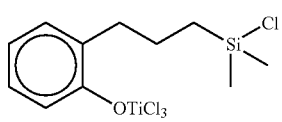

TiCl$_4$ (1.9 g, 10 mmol) was added to solution of 2,2-dimethyl-2,3,4,5-tetrahydro-1,2-benzoxasilepine (1.90 g, 10 mmol) in CH$_2$Cl$_2$/hexane (15+10 mL). The mixture was stirred for 16 h, solution was separated by decantation and evaporated. The residue was recrystallized from hexane yielding the product as dark red crystalline powder.

$^1$H NMR (CDCl$_3$) δ: 0.41 (s, 6H); 0.96 (m, 2H); 1.81 (m, 2H); 2.89 (m, 2H); 7.15 (d, 1H); 7.20 (m, 2H); 7.35 (d, 1H).

$^{13}$C NMR (CDCl$_3$) δ: 1.59; 19.02; 24.42; 33.78; 120.54; 126.81; 127.31; 130.16; 130.21; 131.29.

EXAMPLE 21

Bis(2,6-dimethyl-4-allylphenoxy) dichlorotitanium (IV)

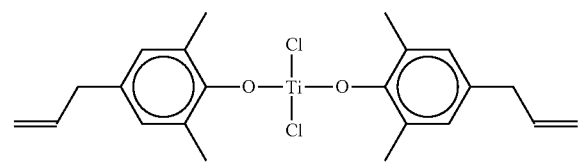

BuLi (1.6M in hexane, 15 mL, 24 mmol) was added at −20° C. to solution of 2,6-dimethyl-4-allylphenol (3.89 g, 24 mmol) in hexane (50 mL). The mixture was allowed to warm to room temperature (crystalline precipitate formed), cooled to −40° C., and TiCl$_4$ (2.28 g, 12 mmol) was added. The reaction mixture was allowed to warm to room temperature and stirred for 16 h. The mixture was filtered, filtrate was concentrated under reduced pressure and dried in vacuo. The yield was 5.2 g (>95%), red viscous oil.

$^1$H NMR (CDCl$_3$) δ: 2.36 (s, 12H); 3.33 (d, 4H); 5.12 (m, 4H); 5.98 (m, 2H); 6.84 (s, 4H).

EXAMPLE 22

Bis(2,6-dimethyl-4-(3-chlorodimethylpropyl)phenoxy) dichlorotitanium (IV)

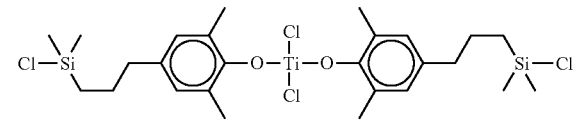

SiHMe₂Cl (0.56 g, 6 mmol) was added to solution of bis(2,6-dimethyl-4-allylphenoxy) dichlorotitanium (IV) (0.95 g, 2.15 mmol) in CH₂Cl₂/hexane (10+5 mL) in the presence of Pt(PPh₃)₂Cl₂. The mixture was stirred for 16 h at 40° C., solution was separated by decantation and evaporated yielding the product as dark red viscous oil.

$^1$H NMR (CDCl₃) δ: 0.40 (s, 12H); 0.82 (m, 4H); 1.67 (m, 4H); 2.29 (s, 12H); 2.53 (t, 4H); 6.76 (s, 4H).

EXAMPLE 23

Bis(2-(3-chlorodimethylpropyl)phenoxy) dichlorotitanium (IV)

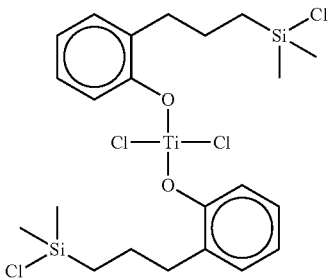

TiCl₄ (0.95 g, 5 mmol) was added to solution of 2,2-dimethyl-2,3,4,5-tetrahydro-1,2-benzoxasilepine (1.92 g, 10 mmol) in CH₂Cl₂/hexane (15+10 mL). The mixture was stirred for 16 h, solution was separated by decantation and evaporated yielding the product as dark red viscous oil.

$^1$H NMR (CDCl₃) δ: 0.38 (s, 12H); 0.90 (m, 4H); 1.78 (m, 4H); 2.83 (t, 4H); 7.06-7.20 (m, 8H).

B. Catalyst Preparation and Testing

EXAMPLE 24

Batch Epoxidation of 1-Octene Using TBHP Oxidate

Supported catalyst was prepared by the following general procedure: A required amount of a metal complex precursor (prepared as indicated above or using methods known in the art) was dissolved in 10 ml of dry CH₂Cl₂ and under N₂ added to a top of a column packed with 2 g of silica gel (MS-3050 of PQ Corporation), calcined overnight at 300° C., and washed with 10 ml of CH₂Cl₂. After drying in a stream of N₂ at 40° C. and tested in 1-octene epoxidation.

An aliquot (14 mL) of a 1-octene solution of 41% tert-butylhydroperoxide (TBHP) in tert-butyl alcohol (4.4 wt. % TBHP in 1-octene) is placed in a round-bottom flask equipped with a magnetic stir bar. The mixture is heated to 80° C. under nitrogen. The epoxidation reaction is started by adding a catalyst sample of specified weight to start the reaction. The reaction continues for 1 h, after which a sample is removed from the flask using a needle with an in-line filter. TBHP content before and after the test is determined by iodometric titration, and the percent of conversion is calculated. Based on these conversion values and catalyst amount the activity of the catalyst is quantified as grams of TBHP reacted per gram of catalyst per hour under the above specified conditions. The selectivity of the epoxidation was determined using GC.

TABLE 1

Results from Batch Epoxidation of 1-Octene using TBHP Oxidate.

| Structure of Precursor Complex | Catalyst # | Activity, g TBHP/gCat/h | Selectivity, % |
|---|---|---|---|
| TiCl4 | 0.5 mmol Ti/SiO₂ (300° C.) | 0.611 | 44.03 |
| [Nb complex with 2,6-diisopropylphenoxy ligands, Cl₃] | 0.5 mmol Ti/SiO₂ (300° C.) | 0.28 | 23 |
| [Nb complex with three 2,6-diisopropylphenoxy ligands, Cl₂] | 0.5 mmol Ti/SiO2 (300° C.) | 0.35 | 20 |

TABLE 1-continued
Results from Batch Epoxidation of 1-Octene using TBHP Oxidate.
| Structure of Precursor Complex | Catalyst # | Activity, g TBHP/gCat/h | Selectivity, % |
|---|---|---|---|
| 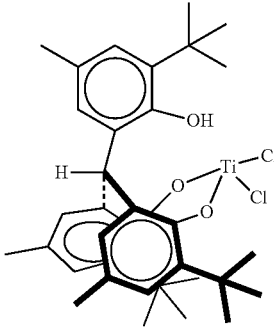 | 0.9 mmol Ti/SiO2 (200° C.)<br>0.45 mmol Ti/SiO2 (300° C.)<br>0.22 mmol Ti/SiO2 (700° C.) | 1.54<br>1.69<br><br>1.59 | 67<br>66<br><br>70 |
| 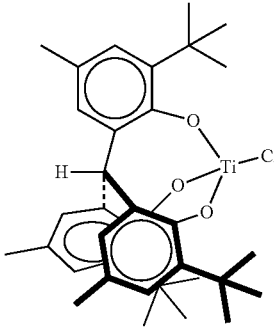 | 0.9 mmol Ti/SiO2 (200° C.) | 1.11 | 64 |
| 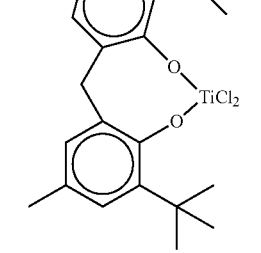 | 0.9 mmol Ti/SiO2 (200° C.) | 0.906 | 94 |
| 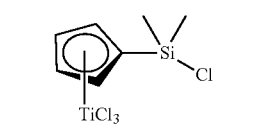 | 0.24 mmol Ti/SiO2 (300° C.) | 0.72 | >90 |
|  | 0.24 mmol Ti/SiO2 (300° C.) | 0.727 | 85 |

TABLE 1-continued

Results from Batch Epoxidation of 1-Octene using TBHP Oxidate.

| Structure of Precursor Complex | Catalyst # | Activity, g TBHP/gCat/h | Selectivity, % |
|---|---|---|---|
| Cp₂Si(Me)₂-Si(Me)₂Cl with TiCl₃ | 0.24 mmol Ti/SiO2 (300° C.) | 1.22 | >95 |
| CpTiCl₃ | 0.24 mmol Ti/SiO2 (300° C.) | 0.32 | 5.4 |
| (PhO)₂TiCl₂ | 0.5 mmol Ti/SiO2 (300° C.) | 1.41 | 96 |
| (2,4,6-tBu₃-C₆H₂O)₂TiCl₂ | 0.5 mmol Ti/SiO2 (300° C.) | 0.53 | 73 |
| (iPrO)₂TiCl₂ | 0.5 mmol Ti/SiO2 (300° C.) | 1.39 | 78 |

EXAMPLE 25

Preparing and Testing of a Silica Supported Catalyst Using 2,2-Dimethyl-2,3,4,5-tetrahydrobenzo[f][1,2]oxasilepine 2 g of MS-3050 silica from PQ Corporation (calcined overnight at 200° C.) was impregnated in a column under an $N_2$ atmosphere with 13 ml 1M $TiCl_4$ solution in toluene. Under $N_2$ flow the temperature was raised to 600° C. and calcined for 2 hours followed by an additional hour of calcination at 600° C. after switching to a dry air flow through the column. The $TiCl_4$ treated silica was transferred to a flask, combined with a 30 ml $CH_2Cl_2$ diluent under $N_2$ atm, followed by addition of 0.378 g of 2,2-dimethyl-2,3,4,5-tetrahydrobenzo[f][1,2]oxasilepine in 10 ml of $CH_2Cl_2$, and left to react over the weekend. The $CH_2Cl_2$ diluent was slowly evaporated and the remaining solid dried in a $N_2$ stream at 50° C.

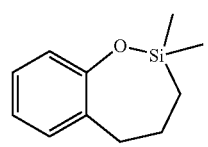

2,2-dimethyl-2,3,4,5-tetrahydrobenzo[f][1,2]oxas-ilepine

Testing of the catalyst using the 1-octene test shows an activity of 3.43 g/g/h at 80° C. and an 85% selectivity.

EXAMPLE 26

Preparing and Testing of a Silica Supported Catalyst Using Bis(dimethyl(vinyl)silyl)amine 2 g of silica from PQ Corporation (calcined over a weekend at 200° C.) was impregnated in a column under $N_2$ atmosphere with 10 ml 1M $TiCl_4$ solution in toluene. Under $N_2$ flow the temperature was raised to 700° C. and calcined for 2 hours and followed by an additional hour of calcination at 700° C. after switching to a dry air flow through the column. After cooling down to ambient temperature the product was washed with 40 ml of MeOH under $N_2$, dried at 200° C. for 2 hours, followed by slow addition of 2 ml of tetrametyldivinylsilazane (bis(dimethyl(vinyl)silyl)amine) in a stream of $N_2$ at 200° C. The temperature was raised to 500° C. and further calcined to crosslink the vinylsilane fragments on the surface.

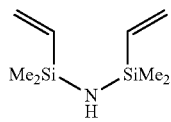

bis(dimethyl(vinyl)silyl)amine

Testing of the catalyst using the 1-octene test shows an activity of 6.65 g/g/h at 80° C. and a 96.7% selectivity.

All of the compounds, complexes, and methods disclosed and claimed herein can be made and executed without undue experimentation in light of the present disclosure. Where the compounds, complexes, and methods of this invention have been described in terms of preferred embodiments, it will be apparent to those of skill in the art that variations may be applied to the compounds, complexes, and methods, as well as in the steps or in the sequence of steps of the method described herein without departing from the concept, spirit, and scope of the invention. More specifically, it will be apparent that certain agents which are chemically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references to the extent that they provide exemplary procedural or other details supplementary to those set forth herein, are specifically incorporated herein by reference.

Anderson, N. G., *Practical Process Research & Development—A Guide For Organic Chemists*, 2nd ed., Academic Press, New York, 2012.
*Hazardous Laboratory Chemicals Disposal Guide*, 3rd edition, by Margaret-Ann Armour, Lewis publishers
*Inorg. Chem.*, 1991, 30, 145-148
*J. Chem. Soc., Perkin Trans.* 1, 200, 1741.
*Org. Lett.*, 2001, 3, 2161.
*Inorg. Chem.*, 1985, 24, 995
*Inorg. Chem.*, 1997, 36, 362
*J. Organomet. Chem.*, 1194, 473, 105
*J. Organomet. Chem.*, 1194, 473, 105

What is claimed is:
1. A method of preparing a catalyst, comprising:
(a) contacting an inorganic siliceous solid with a metal complex of the formula:

(I)

(II)

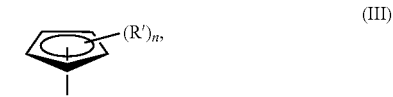

(III)

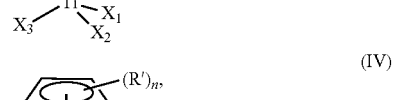

(IV)

(V)

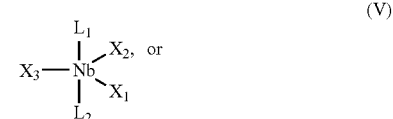

(VI)

wherein:
L$_1$ is alkoxy$_{(C\leq 8)}$, aryloxy$_{(C\leq 16)}$, aralkoxy$_{(C\leq 16)}$, or a substituted version of any of these groups, or L$_1$ is taken together with L$_2$ as defined below, or L$_1$ is taken together with L$_2$ and L$_3$ as defined below;
L$_2$ is alkoxy$_{(C\leq 8)}$, aryloxy$_{(C\leq 16)}$, aralkoxy$_{(C\leq 16)}$, or a substituted version of any of these groups, or L$_2$ is taken together with L$_1$ as defined below, or L$_2$ is taken together with L$_1$ and L$_3$ as defined below;
L$_3$, if present, is alkoxy$_{(C\leq 8)}$, aryloxy$_{(C\leq 16)}$, aralkoxy$_{(C\leq 16)}$, or a substituted version of any of these groups, or L$_3$ is taken together with L$_1$ and L$_2$ as defined below:
L$_1$ and L$_2$, when taken together, are a group of the formula:

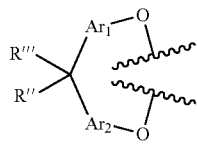

wherein:
R'' and R''' are each independently —H, alkyl$_{(C \leq 8)}$, alkenyl$_{(C \leq 8)}$, alkynyl$_{(C \leq 8)}$, aryl$_{(C \leq 12)}$, aralkyl$_{(C \leq 12)}$, heteroaryl$_{(C \leq 8)}$, heterocycloalkyl$_{(C \leq 12)}$, or a substituted versions of any of these groups other than —H; and Ar$_1$ and Ar$_2$ are each independently arenediyl$_{(C \leq 16)}$ or substituted arenediyl$_{(C \leq 16)}$;

L$_1$, L$_2$ and L$_3$, when taken together, are a group of the formula:

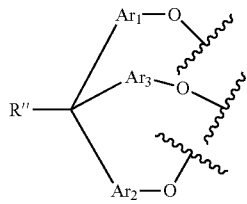

wherein:
R'' is —H, alkyl$_{(C \leq 8)}$, alkenyl$_{(C \leq 8)}$, alkynyl$_{(C \leq 8)}$, aryl$_{(C \leq 12)}$, aralkyl$_{(C \leq 12)}$, heteroaryl$_{(C \leq 8)}$, heterocycloalkyl$_{(C \leq 12)}$, or a substituted versions of any of these groups other than —H; and Ar$_1$, Ar$_2$, and Ar$_3$ are each independently arenediyl$_{(C \leq 16)}$ or substituted arenediyl$_{(C \leq 16)}$;

X$_1$, X$_2$, and X$_3$ are each chloro;

R' is each independently:
—H, —OH, —SH, —CN, —F, —CF$_3$, —NH$_2$, —Si(CH$_3$)$_2$Cl, or —Si(CH$_3$)$_2$—Cp—Si(CH$_3$)$_2$Cl, or alkyl$_{(C \leq 8)}$, alkenyl$_{(C \leq 8)}$, alkynyl$_{(C \leq 8)}$, aryl$_{(C \leq 12)}$, aralkyl$_{(C \leq 12)}$, heteroaryl$_{(C \leq 8)}$, heterocycloalkyl$_{(C \leq 12)}$, or a substituted versions of any of these groups; or two or more pairs of R' are taken together to form an alkenediyl$_{(C \leq 8)}$ or a substituted alkenediyl$_{(C \leq 8)}$; and n is 0 to 5;

to form a metal complex inorganic siliceous solid mixture; and (b) calcining the mixture from step (a) between 200° C. to 400° C. under conditions suitable to form a catalyst comprising the metal from the metal complex attached to the inorganic siliceous solid;

with the proviso that the method does not comprise a calcining step at a temperature greater than 400° C.

2. The method of claim 1, wherein the metal complex is of formula (I).

3. The method of claim 1, wherein the metal complex is of formula (II).

4. The method of claim 1, wherein the metal complex is of formula (III).

5. The method of claim 1, wherein the metal complex is of formula (IV).

6. The method of claim 1, wherein L$_1$, L$_2$, or L$_3$ is aryloxy$_{(C \leq 16)}$.

7. The method of claim 6, wherein L$_1$, L$_2$, or L$_3$ is 2,6-diisopropylphenoxy.

8. The method of claim 6, wherein L$_1$, L$_2$, or L$_3$ is 2,6-di-tert-butyl-(4-methyl)-phenoxy.

9. The method of claim 1, wherein L1, L2, or L3 is alkoxy(C≤8).

10. The method of claim 1, wherein L$_1$, L$_2$, or L$_3$ is isopropoxy.

11. The method of claim 1, wherein L$_1$ and L$_2$ are taken together and are a group of the formula:

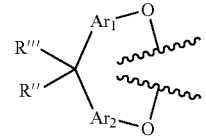

wherein:
R'' and R''' are each independently —H, substituted alkyl$_{(C \leq 8)}$, alkenyl$_{(C \leq 8)}$, or a substituted aryl$_{(C \leq 12)}$; and Ar$_1$ and Ar$_2$ are each independently arenediyl$_{(C \leq 16)}$.

12. The method of claim 1, wherein L$_1$, L$_2$ and L$_3$ are taken together and are a group of the formula:

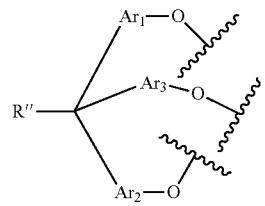

wherein:
R''' is —H or a substituted aryl$_{(C \leq 12)}$; and

Ar$_1$ and Ar$_2$ are each independently arenediyl$_{(C \leq 16)}$.

13. The method of claim 1, wherein R' is —Si(CH$_3$)$_2$Cl.

14. The method of claim 1, wherein step (a) is conducted in the presence of a halogenated hydrocarbon.

15. The method of claim 14, wherein the halogenated hydrocarbon is methylene chloride.

16. The method of claim 1, further comprising a crosslinking step, whereby L$_1$, L$_2$, or L$_3$ attached to a first metal site of the catalyst is connected with an L$_1$, L$_2$, or L$_3$ attached to a second metal site of the catalyst.

17. The method of claim 1, wherein the resulting catalyst has an activity for the epoxidation of 1-octene that is greater than 1.5 grams of tert-butylhydroperoxide (TBHP) reacted per gram of catalyst per hour when 14 mL of 1-octene solution of 41% tert-butylhydroperoxide (TBHP) in tert-butyl alcohol (4.4 wt. % TBHP in 1-octene) is stirred under nitrogen at 80° C.

18. A method of preparing a stabilized catalyst, comprising:

(a) contacting an inorganic siliceous solid with titanium tetrachloride to produce a titanium tetrachloride-impregnated solid;

(b) calcining the titanium tetrachloride-impregnated solid at a temperature from 500° C. to 1000° C. to produce a pre-catalyst;

(c) reacting the pre-catalyst with a compound of the formula:

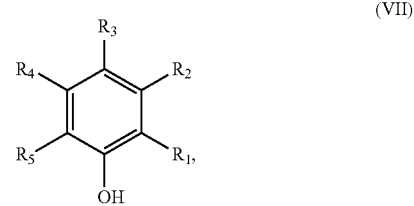

(VII)

-continued

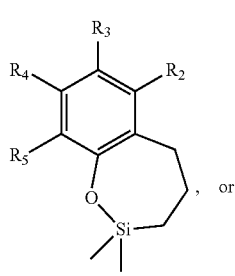
(VIII), or

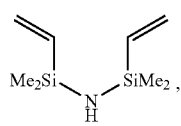
(IX)

wherein:
$R_1$, $R_2$, $R_3$, $R_4$, and $R_5$ are each independently is each independently:
—H, —OH, —SH, —CN, —F, —CF$_3$, —NH$_2$, or —Si(CH$_3$)$_2$Cl; or
alkyl$_{(C≤8)}$, alkenyl$_{(C≤8)}$, alkynyl$_{(C≤8)}$, aryl$_{(C≤12)}$, aralkyl$_{(C≤12)}$, heteroaryl$_{(C≤8)}$, acyl$_{(C≤8)}$, alkoxy$_{(C≤8)}$, aryloxy$_{(C≤12)}$, acyloxy$_{(C≤8)}$, alkylamino$_{(C≤8)}$, dialkylamino$_{(C≤8)}$, amido$_{(C≤8)}$, or substituted versions of any of these groups;
at 100° C. to 300° C. and under conditions suitable for forming the stabilized catalyst.

19. The method of claim 18, wherein $R_1$, $R_2$, $R_3$, $R_4$, and $R_5$ are each —H.

20. The method of claim 18, further comprising a cross-linking step, whereby the stabilized catalyst comprises two or more alkenyl$_{(C≤8)}$ groups that react with one another to form a covalent bond when the catalyst is heated at 400° C. to 800° C.

21. The method of claim 1, wherein the catalyst is selected from the group consisting of:

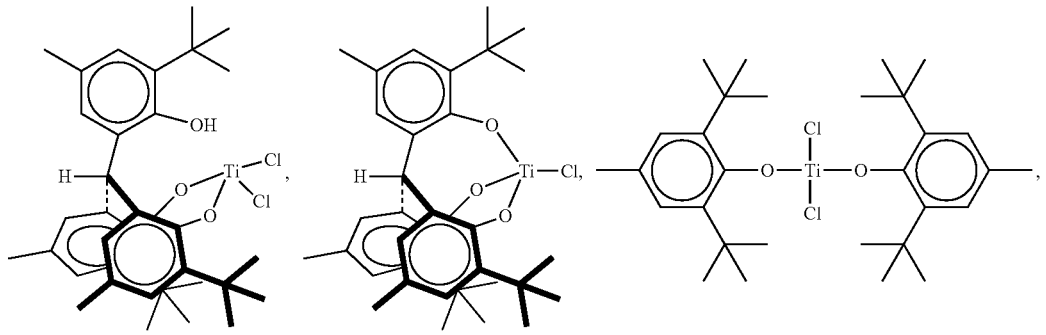

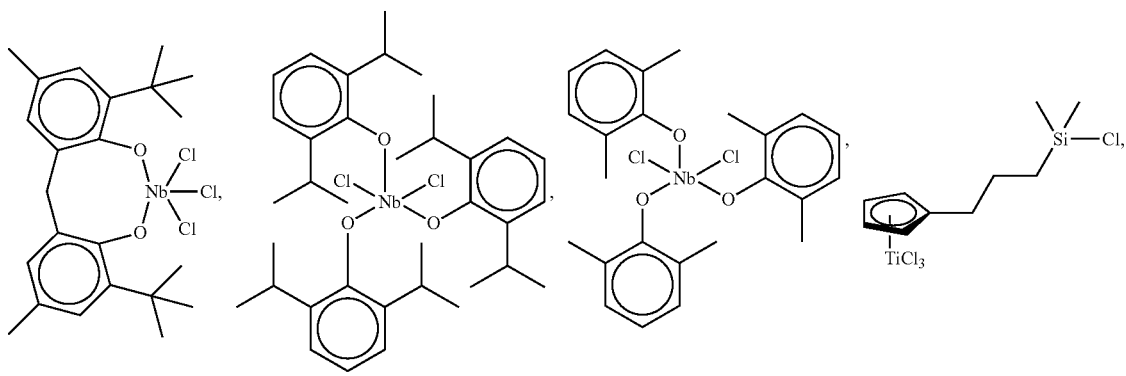

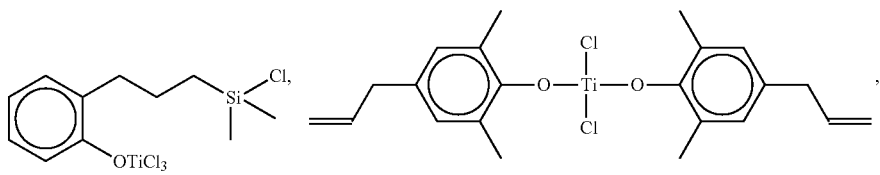

41
-continued
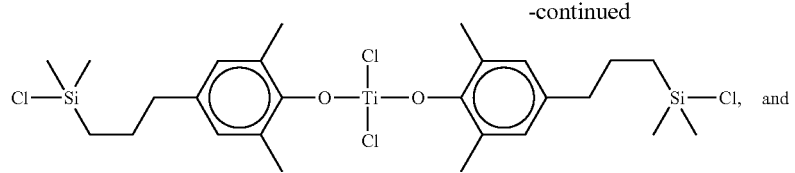
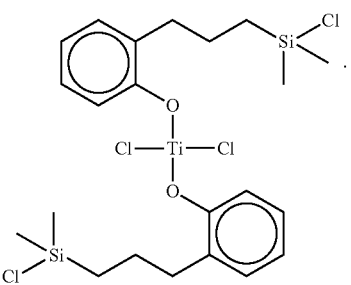
42
22. A compound of the formula:
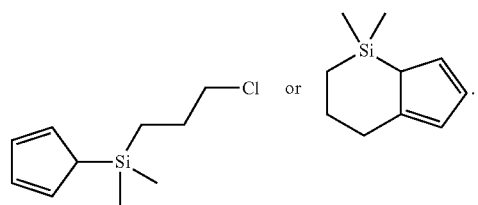
* * * * *

UNITED STATES PATENT AND TRADEMARK OFFICE
CERTIFICATE OF CORRECTION

PATENT NO. : 9,593,134 B2
APPLICATION NO. : 14/801477
DATED : March 14, 2017
INVENTOR(S) : Debra L. Jackson et al.

It is certified that error appears in the above-identified patent and that said Letters Patent is hereby corrected as shown below:

In the Specification

| | | |
|---|---|---|
| Column 4 | Line 28 | After "-OH,", insert -- -SH, -CN,-- |
| Column 6 | Line 63 | After "alkylamino$_{(C\leq8)}$", insert --,-- |
| Column 6 | Line 64 | After "dialkylamino$_{(C\leq8)}$", insert --,-- |
| Column 6 | Line 65 | After "arylamino$_{(C\leq8)}$", insert --,-- |
| Column 18 | Line 1 | Delete "C(O)CH(CH$_3$)$_2$, C(O)CH(CH$_2$)$_2$, C(O)C$_6$H$_5$," and insert -- -C(O)CH(CH$_3$)$_2$, -C(O)CH(CH$_2$)$_2$, -C(O)C$_6$H$_5$,-- |
| Column 19 | Line 7 | Delete "-NH- alkanediyl-, -NH- alkanediyl-NH-," and insert -- -NH-alkanediyl-, -NH-alkanediyl-NH-,-- |
| Column 20 | Line 64 | Delete "HO" and insert --OH-- |
| Column 30 | Line 4 | In Table 1, delete "TiCl4" and insert --TiCl$_4$-- |
| Column 30 | Line 6 | In Table 1, delete "Ti/SiO2" and insert --Ti/SiO$_2$-- |
| Column 31 | Line 4 | In Table 1, delete "Ti/SiO2" and insert --Ti/SiO$_2$-- |
| Column 31 | Line 5 | In Table 1, delete "Ti/SiO2" and insert --Ti/SiO$_2$-- |
| Column 31 | Line 7 | In Table 1, delete "Ti/SiO2" and insert --Ti/SiO$_2$-- |
| Column 31 | Line 9 | In Table 1, delete "Ti/SiO2" and insert --Ti/SiO$_2$-- |
| Column 31 | Line 10 | In Table 1, delete "Ti/SiO2" and insert --Ti/SiO$_2$-- |
| Column 31 | Line 11 | In Table 1, delete "Ti/SiO2" and insert --Ti/SiO$_2$-- |
| Column 31 | Line 13 | In Table 1, delete "Ti/SiO2" and insert --Ti/SiO$_2$-- |
| Column 33 | Line 4 | In Table 1, delete "Ti/SiO2" and insert --Ti/SiO$_2$-- |
| Column 33 | Line 6 | In Table 1, delete "Ti/SiO2" and insert --Ti/SiO$_2$-- |
| Column 33 | Line 8 | In Table 1, delete "Ti/SiO2" and insert --Ti/SiO$_2$-- |
| Column 33 | Line 9 | In Table 1, delete "Ti/SiO2" and insert --Ti/SiO$_2$-- |
| Column 33 | Line 10 | In Table 1, delete "Ti/SiO2" and insert --Ti/SiO$_2$-- |
| Column 35 | Line 67 | Delete "200," and insert --2000,-- |
| Column 36 | Line 4 | Delete "1194," and insert --1994,-- |
| Column 36 | Line 5 | Delete "1194," and insert --1994,-- |

Signed and Sealed this
Twenty-ninth Day of October, 2019

Andrei Iancu
*Director of the United States Patent and Trademark Office*

In the Claims

| | | |
|---|---|---|
| Column 37 | Line 33 | In Claim 1, delete "Cl, or" and insert --Cl; or-- |
| Column 37 | Line 64 | In Claim 9, delete "L1, L2, or L3 is alkoxy(C≤8)." and insert --$L_1$, $L_2$, or $L_3$ is alkoxy$_{(C\leq 8)}$.-- |